(12) United States Patent
Eslami et al.

(10) Patent No.: US 10,117,967 B2
(45) Date of Patent: Nov. 6, 2018

(54) SCAFFOLD FOR SKIN TISSUE ENGINEERING AND A METHOD OF SYNTHESIZING THEREOF

(71) Applicants: Maryam Eslami, Tehran (IR); Parvaneh Reshteh Ahmadi, Tehran (IR); Alireza Eslami, Tehran (IR)

(72) Inventors: Maryam Eslami, Tehran (IR); Parvaneh Reshteh Ahmadi, Tehran (IR); Alireza Eslami, Tehran (IR)

( * ) Notice: Subject to any disclaimer, the term of this patent is extended or adjusted under 35 U.S.C. 154(b) by 0 days.

(21) Appl. No.: 15/729,668

(22) Filed: Oct. 11, 2017

(65) Prior Publication Data

US 2018/0117215 A1    May 3, 2018

(51) Int. Cl.
| | |
|---|---|
| *A61L 27/20* | (2006.01) |
| *A61L 27/18* | (2006.01) |
| *A61L 27/38* | (2006.01) |
| *A61L 27/22* | (2006.01) |
| *C08L 67/02* | (2006.01) |
| *C07K 14/78* | (2006.01) |
| *C12N 5/077* | (2010.01) |
| *C08B 37/08* | (2006.01) |
| *C08J 3/075* | (2006.01) |

(52) U.S. Cl.
CPC ............... *A61L 27/18* (2013.01); *A61L 27/20* (2013.01); *A61L 27/222* (2013.01); *A61L 27/3804* (2013.01); *C07K 14/78* (2013.01); *C08B 37/0072* (2013.01); *C08L 67/025* (2013.01); *C12N 5/0656* (2013.01); *C08J 3/075* (2013.01); *C08L 2203/02* (2013.01)

(58) Field of Classification Search
CPC ............................. A61L 27/20; A61L 27/3804
See application file for complete search history.

(56) References Cited

U.S. PATENT DOCUMENTS

| | | | |
|---|---|---|---|
| 2014/0017284 A1 * | 1/2014 | Yang | ........................ A61F 2/02 424/400 |
| 2016/0282338 A1 * | 9/2016 | Miklas | ................... C12M 21/08 |

* cited by examiner

*Primary Examiner* — Zohreh A Fay
(74) *Attorney, Agent, or Firm* — Barry Choobin; Patent 360

(57) ABSTRACT

The embodiments herein disclose a method of fabricating composite scaffolds for skin tissue regeneration. The methacrylated hyaluronic acid (HAMA) and methacrylated gelatin (GelMA) are synthesized. The poly (glycerol sebacate)-poly(ε-caprolactone) (PGS-PCL) microfibrous scaffolds are synthesized. The hydrogel is synthesized. The composite scaffold comprising hydrogel and poly (glycerol sebacate)-poly(ε-caprolactone) (PGS-PCL) microfibrous scaffolds is fabricated. A plurality of physico-chemical characteristics of the composite scaffold comprising hydrogel and poly (glycerol sebacate)-poly(ε-caprolactone) (PGS-PCL) microfibrous scaffolds are analysed. The physico-chemical characteristics comprises mechanical properties, swelling ratio and enzymatic degradation and scanning electron microscope imaging. The fibroblast cells are encapsulated within the composite scaffold comprising hydrogel and poly (glycerol sebacate)-poly(ε-caprolactone) (PGS-PCL) microfibrous scaffolds and hydrogels. The fibroblast cells are seeded on composite scaffold and PGS-PCL scaffold. The fibroblast cell viability, fibroblast cell attachment, fibroblast cell spreading, fibroblast cell proliferation and fibroblast cell metabolism are analysed in composite scaffolds, PGS-PCL scaffolds and hydrogels.

12 Claims, 14 Drawing Sheets

SCAFFOLD FOR SKIN TISSUE ENGINEERING AND A METHOD OF SYNTHESIZING THEREOF

SPONSORSHIP STATEMENT

The present invention is sponsored by Applied Biotechnology Research Center, Tehran Medical Sciences Branch, Islamic Azad University, for international filing.

BACKGROUND

Technical field

The embodiments herein generally relate to the field of tissue engineering. The embodiments herein particularly relate to fabrication of scaffolds for skin tissue regeneration. The embodiments herein more particularly relate to fabrication of fiber reinforced hydrogel scaffold for skin tissue engineering.

Description of the Related Art

Wounds are defined as disruption of any tissue or cellular integrity due to mechanical, physical or metabolism (mainly due to diabetes mellitus) related injuries. In response to the injury or as a recovery or healing process, the major priority is to stop hemorrhage, to avoid excessive blood loss, and prevent microbial infection by infiltration of immune cells, such as neutrophils or macrophages. More importantly, it is critical to restore the function of the damaged tissue or cell through rapid healing. Wound healing is a stepwise process which includes (1) an inflammatory stage characterized by macrophage or leucocytes infiltration and cytokine production; (2) a proliferative phase which includes removal of damaged tissue and formation of granulation tissue in the wound; (3) a maturation phase wherein extracellular matrix produced by the proliferative tissue becomes well-defined; and (4) the formation of scar tissue indicating the completion of the wound healing process. The process of wound healing is more or less similar in all types of tissues, including skin tissue. In particular, skin tissue wounds are categorized as epidermal, dermal or dermo-epidermal, based on the degree and intensity of such wounds. The molecular mechanism of skin wound healing mainly involves production of various growth factors, such as epidermal growth factors (EGF) and tissue growth factors alpha and beta (TGF-$\alpha$, TGF-$\beta$), etc. The conventional approaches used for instant healing of skin wounds include the use of natural products that have anti-inflammatory, anti-microbial and antioxidant properties, such as turmeric (active component curcumin), honey, etc. Hot or cold fomentation at the wound site may reduce inflammation and fasten the healing process.

In the recent few years, the field of regenerative tissue engineering has emerged as a gold standard platform for the development of artificial tissues and organ regeneration, to resolve major health related issues in humans. Multiple disciplines, such as cell biology, biomaterial research, bioengineering, etc., have contributed to the flourishing advances of tissue engineering. The major principle of tissue engineering is to restore and improve the function of the tissues by either generating novel or biocompatible substitutes or by reconstruction of the tissues. Use of cells or cell implants, delivery of tissue growth enhancing factors and use of various matrices, such as scaffolds to generate three dimensional (3D) cellular structures are the three major pioneering approaches of tissue regenerative medicine.

Over the past several years, skin tissue regeneration has shown promise due to the invention of several novel skin tissue engineered products. A plurality of (allograft, autograft, xenograft) grafts of dermal, epidermal or dermo-epidermal origin have been reported and have been used commercially. Such grafts help restore the structure of the skin tissue by repairing the wound effectively.

Such bioengineered skin substitutes not only repair the wounds, but also have various supplements, such as growth factors, antibiotics and anti-inflammatory drugs which eventually fasten the wound healing process. To engineer these substitutes, various scaffold matrices have been developed to promote cell growth in 3D structure. Such scaffolds are highly biocompatible with skin tissue and biodegradable in nature, acting as suitable dressing material for wound healing. Recent advances in the skin tissue engineering field revolve around the use of scaffolds with cell population, such as keratinocytes and fibroblasts.

A biomaterial is a material that is fabricated to interact with biological systems. Biomaterials can take many forms including a homogenous material, a blended material, or composite material. Often such biomaterials are designed to have usefulness in the medical field for diagnostic as well as therapeutic purposes. Biomaterials can be fabricated from natural as well as synthetic materials. Biomaterials can include polymers, metals, ceramics, and many other materials.

A plurality of scaffolds are fabricated for tissue regeneration and tissue engineering. These scaffolds provide a template on which cells can migrate, divide, secrete new matrix and differentiate. Typical tissue engineering scaffolds are porous and are categorized as having pores on either a micrometer scale, i.e. microporous, or a nanometer scale, i.e. nanoporous. Scaffolds having pores on a micrometer scale, or having average pore diameter of about 10 to 1000 microns, are composed of a variety of biocompatible materials including metals, ceramics and polymers. Such scaffolds include solid-cast structures, open-pore foams, felts, meshes, nonwovens, woven and knitted constructs. The mechanical and conformational properties are chosen by composition of the material and the design of the scaffold. The desirable mechanical properties include the ability to be sutured in place and good handling strength.

Composition, design and construction of the scaffold are also important to how tissue responds to the scaffold. The scaffold is shaped to maximize surface area, to allow adequate diffusion of nutrients and growth factors to cells present in or growing into it. A scaffold must be configured with pores on a micrometer scale. The pores provide enhanced surface area for the cells to be nourished by diffusion until new blood vessels interdigitate the implanted scaffold.

The scaffolds having pores on a nanometer scale, e.g. having average pore diameter of about 10 nanometers to 1 micron, are often composed of hydrogels. A hydrogel is a substance formed when a natural or synthetic organic polymer is cross-linked via covalent, ionic or hydrogen bonds to create a three-dimensional open-lattice structure, which entraps water molecules and forms a gel. Examples of materials that can be used to form a hydrogel include polyamides, methylcellulose, collagen, extracellular matrix (ECM), polysaccharides such as alginate, polyphosphazines, polyacrylates which are crosslinked tonically, high molecular weight poly (oxyalkylene ether), nonionic polymerized alkylene oxide compounds, or polyethylene oxide-polypropylene glycol block copolymers.

Hydrogels provide conformable, malleable, or injectable materials for administering cells into a tissue. They do not, however, have mechanical integrity. Synthetic hydrogels are sterilized and do not have the risk of associated infectious agents. However, most synthetic hydrogels do not mimic the extracellular matrix and therefore do not direct cellular ingrowth or function. Hydrogels of natural extracellular matrix are biocompatible and can mimic the native cellular environment. However, natural hydrogels, unless made from autologous material, may elicit an immune response and may have associated infectious agents. Natural hydrogels, such as EHS mouse sarcoma basement membrane, or fibrin, have a fiber diameter of about 5 to about 10 nanometers, water content of about 80 to about 97 wt % and average pore diameter of about 50 to about 400 nm.

Among the recent technologies in the multidisciplinary field of tissue engineering or regenerative medicine, use of various types of scaffolds is the key component. In tissue engineering, scaffolds are the best materials for restoring, maintaining and improving tissue function. They play a unique role in repair and more importantly regeneration of tissues by providing a suitable platform, permitting essential supply of various factors associated with survival, proliferation and differentiation of cells. Scaffolds can be made up of synthetic or absorbable, naturally occurring, biological, degradable or non-degradable polymeric materials. Several techniques have been used to construct scaffolds but the four major scaffolding approaches include the use of ECM secreting cell sheets, pre-made porous scaffolds of synthetic, natural and biodegradable biomaterials, decellularized ECM scaffolds, and cells entrapped in hydrogels. All these approaches have advantages as well as drawbacks. In this review, we intend to focus on the different types of scaffolds based on their biomaterial design and their advantages/disadvantages, especially those scaffolds which are extensively used for skin tissue regeneration.

The biomaterials are either natural or synthetic or a combination of both (composite scaffolds). Due to their resemblance to the natural extracellular matrix (ECM), biocompatibility, and biodegradability, natural polymers are widely used in wound and burn dressing. Natural polymers used in skin regeneration are of protein or carbohydrate origin. These polymers stimulate the healing by repair of the damaged tissue and promote effective skin regeneration. The synthetic polymers are fabricated mainly using electrospinning with controlled degradation characteristics and architecture.

Hyaluronic acid (HA) is a natural, non-sulfated glycosaminoglycan that plays an important role in skin morphogenesis and wound repair. HA and its derivatives have been widely used as hydrogels for tissue engineering due to its inherent biocompatibility and biodegradability characteristics, as well as their gel-forming properties. Using HA as a skin tissue engineering material could provide key advantages because it has been known to promote elastin secretion in valvular interstitial cells. Furthermore, HA can be methacrylated (HAMA) and thus can be rendered photocrosslinkable upon UV exposure. However, HA alone does not promote cell spreading; thus, combining HAMA and methacrylated gelatin (GelMA) could provide a more suitable microenvironment for the cells. However, these hydrogels lack the structural integrity necessary for skin formation. The mechanical shortcomings of the hydrogel structure can be addressed by adding a microfibrous component to reinforce the structure and to provide contact guidance, which is essential for directing the internal organization of the cells.

The fibrous scaffolds can be produced by electrospinning, resulting in a highly porous structure that retains desirable mechanical properties such that it can accommodate directional tensile loads while maintaining mechanical flexibility. However, the high porosity of the PGS-PCL microfibrous scaffolds allows seeded cells to migrate out of the structure. Furthermore, cells tend to attach only on the surface of the scaffold, which makes producing fully cellularized 3D structures difficult.

Hence there is a need to fabricate a composite biomaterial which combines extracellular matrix (ECM) mimicking hydrogels and elastomeric and elastomers poly (glycerol sebacate)-poly (ε-caprolactone) (PGS-PCL) electrospun (ES) scaffolds to mimic the cellular environment and mechanical properties of the native skin tissue. Also, there is a need for a hydrogel composite scaffold for retaining cells within the composite structures, while PGS-PCL component provides mechanical strength and a porous structure to support tissue growth.

The above-mentioned shortcomings, disadvantages and problems are addressed herein and which will be understood by reading and studying the following specification.

OBJECTIVES OF THE EMBODIMENTS

The primary objective of the embodiment herein is to integrate electrospun poly (glycerol sebacate) (PGS)-poly (ε-caprolactone) (PCL microfiber scaffolds, which possess enhanced mechanical properties for skin tissue engineering, within a hybrid hydrogel made from methacrylated hyaluronic acid and methacrylated gelatin.

Another object of the embodiment herein is to provide a composite biomaterial which combines the properties of extracellular matrix, mimicking hydrogels and elastomers poly (glycerol sebacate)-poly (ε-caprolactone) (PGS-PCL) electrospun (ES) scaffolds to mimic the cellular environment and mechanical properties of the skin tissue.

Yet another object of the embodiment herein is to provide a hydrogel composite scaffold for retaining cells within the composite structures, while PGS-PCL component provides mechanical strength and a porous structure to support tissue growth.

Yet another object of the embodiment herein is to utilize extracellular matrix to test the suitability of the composites physical and mechanical properties for skin tissue engineering by analyzing a plurality of physiochemical parameters i.e. swelling ratio, stiffness, porosity, in vitro enzymatic degradation behavior and in vitro analysis.

Yet another object of the embodiment herein is to encapsulate fibroblast cells into the hydrogel.

Yet another object of the embodiment herein is to evaluate fibroblast cells encapsulated in hydrogel, PGC-PCL scaffold and composite scaffold conditions.

Yet another object of the embodiment herein is to illustrate that the presence of PGS in PGS-PCL scaffolds promotes ECM secretion.

Yet another object of the embodiment herein is to illustrate that the hydrogel component provides an environment to encapsulate cells in 3D environment without significantly reducing the mechanical properties of the PGS-PCL structures and the fibrous components provide mechanical properties to the composite.

Yet another object of the embodiment herein is to illustrate that the composite is a 3D gel based cell carrier, and without comprising the mechanical properties.

Yet another object of the embodiment herein is to illustrate that the composite is more easily remodeled and degradable.

Yet another object of the embodiment herein is to illustrate that the composite contains natural polymers.

Yet another object of the embodiment herein is to illustrate that by adding the hydrogel within and around the microfibers producing ECM-like microenvironment, and wherein the hydrogel fully penetrates the pores of fibers.

Yet another object of the embodiment herein is to illustrate that the encapsulated cells are homogenously distributed.

These objects and the other advantages of the embodiments herein will become readily apparent from the following detailed description taken in conjunction with the accompanying drawings.

SUMMARY

The various embodiments herein provide a composite biomaterial which combines the properties of extracellular matrix, mimicking hydrogels and elastomers poly (glycerol sebacate)-poly (ε-caprolactone) (PGS-PCL) electrospun (ES) scaffolds to mimic the cellular environment and mechanical properties of the native skin tissue. The embodiments herein integrate electrospun poly (glycerol sebacate) (PGS)-poly (ε-caprolactone) (PCL) microfiber scaffolds, which possess enhanced mechanical properties for skin tissue engineering, within a hybrid hydrogel made from methacrylated hyaluronic acid and methacrylated gelatin. The hydrogel composite scaffold retains cells within the composite structures, while PGS-PCL component provides mechanical strength and a porous structure to support tissue growth.

According to one embodiment herein, the method of fabricating composite scaffolds for skin tissue regeneration comprises the following steps. The methacrylated hyaluronic acid (HAMA) and methacrylated gelatin (GelMA) are synthesized. The poly (glycerol sebacate)-poly (ε-caprolactone) (PGS-PCL) microfibrous scaffolds are synthesized. The hydrogel (hydrogel precursor solution) is synthesized. The hydrogel is synthesized from hyaluronic acid (HAMA) and methacrylated gelatin (GelMA). The composite scaffold comprising hydrogel and poly (glycerol sebacate)-poly(ε-caprolactone) (PGS-PCL) microfibrous scaffolds is fabricated. The fibroblast cells are cultured in predetermined conditions. The fibroblast cells are encapsulated within the composite scaffold comprising hydrogel and the poly (glycerol sebacate)-poly(ε-caprolactone) (PGS-PCL) microfibrous scaffolds and within the hydrogels separately. The hydrogel with encapsulated fibroblast cells is used to compare the fibroblast cell viability with composite scaffolds. The fibroblast cells are seeded on composite scaffold and PGS-PCL scaffold separately. The PGS-PCL scaffold used to compare the fibroblast cell viability with composite scaffolds. The poly (glycerol sebacate)-poly(ε-caprolactone) (PGS-PCL) microfibrous scaffolds and the poly(ε-caprolactone) (PCL) microfibers are soaked in the hydrogel precursor solution. The poly(ε-caprolactone) (PCL) microfibres are control. The soaking of the hydrogel into the PGS-PCL microfibres is analysed and imaged to analyse the imbibition of hydrogel in the PGS-PCL microfibres and PCL microfibres. A plurality of physico-chemical characteristics of the composite scaffold comprising hydrogel and poly (glycerol sebacate)-poly(ε-caprolactone) (PGS-PCL) microfibrous scaffolds are analysed. The physico-chemical characteristics comprises mechanical properties, swelling ratio and enzymatic degradation and a structural analysis by scanning electron microscope imaging. The fibroblast cell viability, fibroblast cell attachment, fibroblast cell spreading, fibroblast cell proliferation and fibroblast cell metabolism is analysed in composite scaffolds, PGS-PCL scaffolds and hydrogels.

According to one embodiment herein, the step of synthesizing methacrylated hyaluronic acid (HAMA) and methacrylated gelatin (GelMA), comprises the following steps. A predetermined amount of hyaluronic acid sodium salt is dissolved in de-ionized water. The hyaluronic acid sodium salt is dissolved in de-ionized water to obtain a final concentration of 1% w/v. An optimum pH of the hyaluronic acid sodium salt and de-ionized water solution is monitored and maintained. The methacrylic anhydride is added dropwise to the solution comprising hyaluronic acid sodium salt and de-ionized water to obtain a solution mixture. A pH of 8 is maintained for the solution mixture of hyaluronic acid sodium salt, de-ionized water and methacrylic anhydride. The solution mixture is incubated on ice for a predetermined time period. The pH is monitored at regular interval of time. The pH of the solution mixture is maintained at 8. The solution mixture is agitated for 24 hours in a cold room. A temperature of the cold room is maintained at 4° C. The solution mixture is dialyzed for two days in distilled water. The plurality of solutions are obtained from dialysis. The plurality of solutions obtained from dialysis are changed using 12-14 kDa molecular weight cut-off (MWCO) dialysis tubes. The plurality of solutions are lyophilized for one week to obtain methacrylated hyaluronic acid. The methacrylated hyaluronic acid is stored at −80° C.

According to one embodiment herein, the step of synthesizing metharylated gelatin (GelMA), comprises the following steps. The porcine skin type A gelatin is mixed in Dulbecco's phosphate-buffered saline (DPBS) to obtain a gelatin solution. The gelatin solution is incubated at 60° C. for dissolving the porcine skin type A gelatin in Dulbecco's phosphate-buffered saline (DPBS). The methacrylated anhydride is added dropwise in the gelatin solution to obtain an emulsion. The methacrylated anhydride has a concentration of 0.8 ml/g. The emulsion comprising gelatin and methacrylic anhydride is agitated at a temperature of 60° C. for a time period of 1 hour. The warm DPBS is added to the emulsion for inhibiting a reaction within the emulsion to obtain a mixture. The temperature of DPBS is 40° C. The concentration of DPBS is 2×. The mixture comprising gelatin, methacrylic anhydride and DPBS is dialyzed for 1 week in distilled water using MWCO dialysis tubes. A plurality of solutions are obtained from dialysis. The plurality of solution obtained after dialysis are frozen for a period of 1 week to obtain a white and porous foam of metharylated gelatin (GelMA). The foam of metharylated gelatin (GelMA) is incubated at a temperature of −80° C.

According to one embodiment herein, the step of synthesizing poly (glycerol sebacate)-poly(ε-caprolactone) (PGS-PCL) microfibrous scaffolds, comprises the following steps. A frame is fabricated. The frame comprises a copper wire covered with a non-adhesive tape with a glass slide on top. The poly (glycerol sebacate) and poly(ε-caprolactone) polymers in a predetermined ratio are dissolved in an anhydrous chloroform-ethanol solvent to obtain a solution. The ratio of poly (glycerol sebacate) and poly(ε-caprolactone) is 2:1. The solution comprising poly (glycerol sebacate)-poly(ε-caprolactone) polymers and anhydrous chloroform-ethanol solvent is subjected to electrospinning at 12.5 kV. A concentration of total polymer is 33% w/v. A distance of 10 cm is maintained between electrospinning needle and collector to obtain poly (glycerol sebacate)-poly(ε-caprolactone) (PGS-PCL) microfibrous scaffolds. The dimensions of the needle is 21 gauge. A flow rate of 2 ml/hour is maintained in the elelctrospinning machine. The poly (glycerol sebacate)-poly (ε-caprolactone) (PGS-PCL) microfibrous scaffolds are dried for 24 hours in a vacuum desiccator for removing residual solvents.

According to one embodiment herein, the step of synthesizing hydrogel (hydrogel precursor solution), comprises the following steps. The methacrylated gelatin (GelMA) and methacrylated hyaluronic acid (HAMA) are mixed with endothelial basal medium to obtain a solution. The photoinitiator is added in the solution for obtaining a mixture. The concentration of the photoinitiator is 0.1% v/w. The photoinitiator crosslinks the solution. The photoinitiator is 2-hydroxy-1-(4-(hydroxyethoxy)phenyl)-2-methyl-1-propanone. The mixture is exposed to UV light for a time period of 45 second at 2.6 mW/cm$^2$. A wavelength of UV light is 408 nm. A hydrogel or hydrogel precursor solution is obtained with an initial solution volume of 20 µl. The diameter of the hydrogel is 6 mm. The thickness of the hydrogel is 0.5 mm. The hydrogel or hydrogel precursor is used for the synthesis/fabrication of composite scaffolds. The step of fabricating composite scaffold comprising hydrogel and poly (glycerol sebacate)-poly(ε-caprolactone) (PGS-PCL) microfibrous scaffolds, comprises the following steps. The poly (glycerol sebacate)-poly(ε-caprolactone) (PGS-PCL) microfibrous scaffolds are arranged to obtain scaffolds of 6 mm diameter. The poly (glycerol sebacate)-poly(ε-caprolactone) (PGS-PCL) microfibrous scaffolds are arranged in sheets. The hydrogel is added in the poly (glycerol sebacate)-poly(ε-caprolactone) (PGS-PCL) microfibrous scaffolds. The amount of the hydrogel is 20 ml. The concentration of the photoinitiator in the hydrogel is 0.1%. The poly (glycerol sebacate)-poly(ε-caprolactone) (PGS-PCL) microfibrous scaffolds absorb the hydrogel. The poly (glycerol sebacate)-poly(ε-caprolactone) (PGS-PCL) microfibrous scaffolds and the hydrogel are exposed for crosslinking. The poly (glycerol sebacate)-poly(ε-caprolactone) (PGS-PCL) microfibrous scaffolds and the hydrogel are exposed to UV light for a time period of 45 second at 2.6 mW/cm2. The wavelength of UV light is 408 nm. The composite scaffold comprises elelctrospun poly(glycerol sebacate)-poly(ε-caprolactone) (PGS-PCL) microfibrous scaffold within a hybrid hydrogel comprising methacrylated hyaluronic acid and methacrylated gelatin.

According to one embodiment herein, the step of encapsulating fibroblast cells within the composite scaffold comprising hydrogel and poly (glycerol sebacate)-poly(ε-caprolactone) (PGS-PCL) microfibrous scaffolds and hydrogels, comprises the following steps. The fibroblast cells are cultured in a culture medium supplemented with 10% fetal bovine serum and 1% Penicillin-Streptomycin in predetermined atmospheric conditions. The predetermined atmospheric conditions comprises a temperature of 37° C. and carbon dioxide at a concentration of 5%. The fibroblast cells are cultured/grown on gelatin coated flasks. The fibroblast cells are passaged weekly. The fibroblast cells are trypsinized. The fibroblast cells are re-suspended in a hydrogel precursor solution at a predetermined concentration. The hydrogel precursor solution comprises methacrylated gelatin (GelMA) and methacrylated hyaluronic acid (HAMA) and photoinitiator. The concentration of photoinitiator is 0.1% w/v. The concentration of fibroblast cells suspended is 6×10$^6$ cells/ml. The composite scaffolds and the hydrogel precursor with fibroblast cells are exposed to UV light for a time period of 45 second at 2.6 mW/cm2. The wavelength of UV light is 408 nm. The composite scaffolds and hydrogel precursor solution with fibroblast cells are incubated in a culture medium for a time period of 21 days in predetermined conditions. The composite scaffold comprises hydrogel and poly (glycerol sebacate)-poly(ε-caprolactone) (PGS-PCL) microfibrous scaffolds. The culture medium is changed every 30 minutes for first two hours. The cultured medium is changed every 30 minutes for removing photoinitiator.

According to one embodiment herein, the step of seeding fibroblast cells on composite scaffold and PGS-PCL scaffold, comprises the following steps. The composite scaffolds and PGS-PCL scaffolds are sterilized by immersion in 70% ethanol for 2 hours. The composite scaffold comprises poly (glycerol sebacate)-poly(ε-caprolactone) (PGS-PCL) microfibrous scaffolds and hydrogels. The sterilized composite scaffolds and PGS-PCL scaffolds are exposed to UV radiation for a predetermined time. The sterilized composite scaffolds and PGS-PCL scaffolds are washed with DPBS medium. The fibroblast cells are selected at a concentration of 2×10$^4$ cells/scaffold. A predetermined volume of fibroblast cells suspension is added on the composite scaffolds and PGS-PCL scaffolds placed in a 48-well culture plate. The predetermined volume of fibroblast cells is 20 µl. The 48 well plate comprising the composite scaffolds and PGS-PCL scaffolds with fibroblast cell suspension is incubated for a time period of 1 hour. The fibroblast cells are attached to the composite scaffolds and PGS-PCL scaffolds in incubation. The culture medium is changed every day.

According to one embodiment herein, the step of soaking the poly (glycerol sebacate)-poly(ε-caprolactone) (PGS-PCL) microfibrous scaffolds and the poly(ε-caprolactone) (PCL) fibres in the hydrogel precursor solution, comprises the following steps. The PGS-PCL scaffolds and the PCL scaffolds are synthesized. The size of the PGS-PCL scaffolds and PCL scaffolds is 6 mm diameter. The PCL scaffolds are negative control. The 20 µl of the hydrogel solution is added on the PGS-PCL scaffolds and the PCL scaffolds. The PGS-PCL fibres and the PCL fibres are soaked with hydrogel for a predetermined amount of time. The hydrogel with PGS-PCL fibres and the PCL fibres is imaged to analyse the imbibition of hydrogel in the PGS-PCL fibres and PCL fibres. The poly (glycerol sebacate) (PGL) component facilitates the penetration and imbibition of the hydrogel in the PGS-PCL microfibers. The PCL microfiber illustrate less absorption and imbibition of hydrogel when compared to the PGS-PCL microfibers. The imaging illustrates that the hydrogel penetrates into the PGS-PCL microfibers.

According to one embodiment herein, the analysis of a plurality of physico-chemical characteristics of the composite scaffold, PGS-PCL scaffold and hydrogel scaffold illustrate that the composite scaffold comprising hydrogel and poly (glycerol sebacate)-poly(ε-caprolactone) (PGS-PCL) microfibrous scaffolds has hydrophilic property. The hydrophilic property is imparted by the PGS-PCL component. The swelling ratio in the composite scaffold increased ($p<0.05$) after UV exposure.

According to one embodiment herein, the analysis of fibroblast cell viability, fibroblast cell attachment, fibroblast cell spreading, fibroblast cell proliferation and fibroblast cell metabolism in the composite scaffolds, PGS-PCL scaffolds and hydrogels illustrate that the fibroblast cells are spread in the composite hydrogel unevenly. The fibroblast cells are spread evenly in the hydrogel scaffold. The fibroblast cells are spread on the surface of PGS-PCL scaffold. The cell viability of fibroblast cell is above 90% in hydrogel, PGS-PCL scaffold and composite scaffolds. The fibroblast cells illustrate a high metabolic activity in composite scaffold when compared with the fibroblast cells present in PGS-PCL scaffold and hydrogel scaffold.

According to one embodiment herein, the hydrogel component of the composite scaffold provides an extracellular mimicking environment for fibroblast cells. The hydrogel component provides an ability of fibroblast cell delivery to an affected skin tissue. The PGS-PCL component of the composite scaffold facilitate a distribution of the fibroblast cells within the hydrogel component. The PGS-PCL component provides mechanical support to the composite scaffold.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
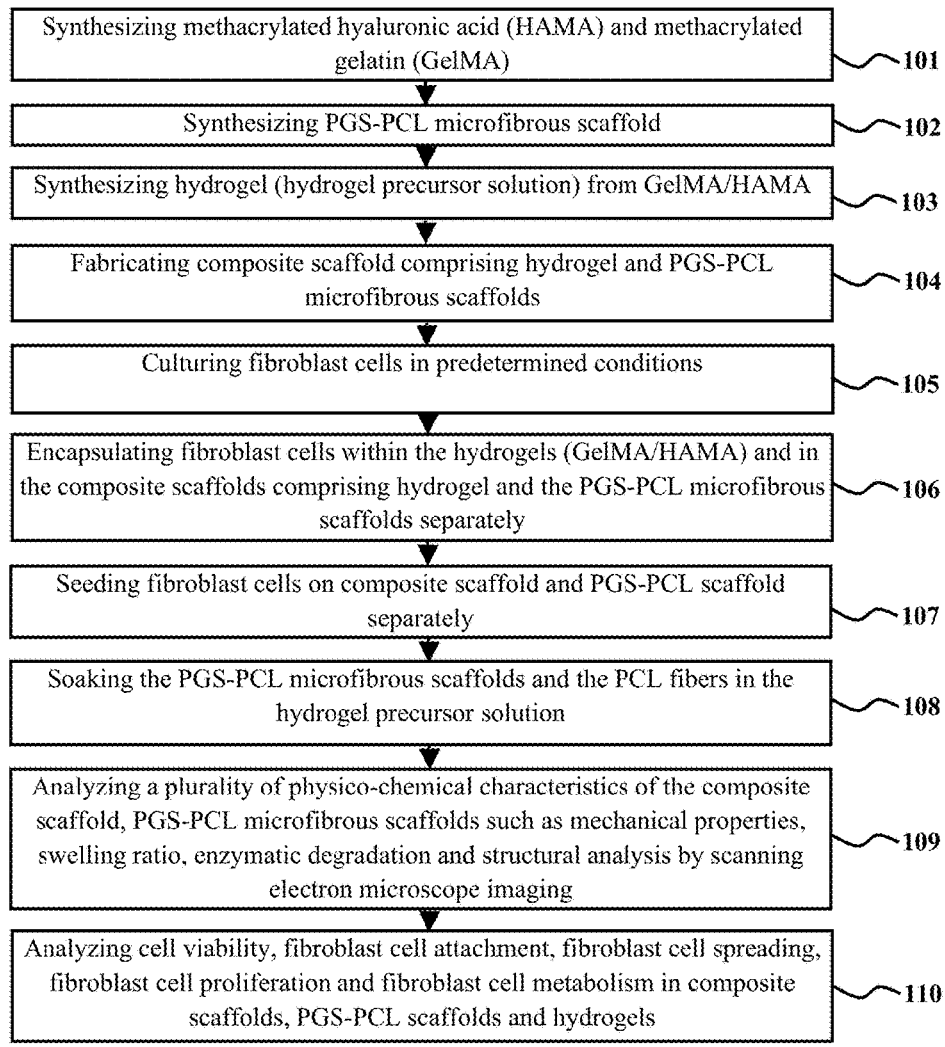
FIG. 1 illustrates a flowchart indicating an overall method of fabricating and analyzing scaffolds for skin tissue regeneration, according to one embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a composite biomaterial which combines the properties of extracellular matrix, mimicking hydrogels and elastomers poly (glycerol sebacate)-poly (ε-caprolactone) (PGS-PCL) electrospun (ES) scaffolds to mimic the cellular environment and mechanical properties of the native skin tissue. The embodiments herein integrate electrospun poly (glycerol sebacate) (PGS)-poly (ε-caprolactone) (PCL) microfiber scaffolds, which possess enhanced mechanical properties for skin tissue engineering, within a hybrid hydrogel made from methacrylated hyaluronic acid and methacrylated gelatin. The hydrogel composite scaffold retains cells within the composite structures, while PGS-PCL component provides mechanical strength and a porous structure to support tissue growth.

According to one embodiment herein, the method of fabricating composite scaffolds for skin tissue regeneration comprises the following steps. The methacrylated hyaluronic acid (HAMA) and methacrylated gelatin (GelMA) are synthesized. The poly (glycerol sebacate)-poly (ε-caprolactone) (PGS-PCL) microfibrous scaffolds are synthesized. The hydrogel (hydrogel precursor solution) is synthesized. The hydrogel is synthesized from hyaluronic acid (HAMA) and methacrylated gelatin (GelMA). The composite scaffold comprising hydrogel and poly (glycerol sebacate)-poly(ε-caprolactone) (PGS-PCL) microfibrous scaffolds is fabricated. The fibroblast cells are cultured in predetermined conditions. The fibroblast cells are encapsulated within the composite scaffold comprising hydrogel and the poly (glycerol sebacate)-poly(ε-caprolactone) (PGS-PCL) microfibrous scaffolds and within the hydrogels separately. The hydrogel with encapsulated fibroblast cells is used to compare the fibroblast cell viability with composite scaffolds. The fibroblast cells are seeded on composite scaffold and PGS-PCL scaffold separately. The PGS-PCL scaffold used to compare the fibroblast cell viability with composite scaffolds. The poly (glycerol sebacate)-poly(ε-caprolactone) (PGS-PCL) microfibrous scaffolds and the poly(ε-caprolactone) (PCL) microfibers are soaked in the hydrogel precursor solution. The poly(ε-caprolactone) (PCL) microfibres are control. The soaking of the hydrogel into the PGS-PCL microfibres is analysed and imaged to analyse the imbibition of hydrogel in the PGS-PCL microfibres and PCL microfibres. A plurality of physico-chemical characteristics of the composite scaffold comprising hydrogel and poly (glycerol sebacate)-poly(ε-caprolactone) (PGS-PCL) microfibrous scaffolds are analysed. The physicochemical characteristics comprises mechanical properties, swelling ratio and enzymatic degradation and a structural analysis by scanning electron microscope imaging. The fibroblast cell viability, fibroblast cell attachment, fibroblast cell spreading, fibroblast cell proliferation and fibroblast cell metabolism is analysed in composite scaffolds, PGS-PCL scaffolds and hydrogels.

According to one embodiment herein, the step of synthesizing methacrylated hyaluronic acid (HAMA) and methacrylated gelatin (GelMA), comprises the following steps. A predetermined amount of hyaluronic acid sodium salt is dissolved in de-ionized water. The hyaluronic acid sodium salt is dissolved in de-ionized water to obtain a final concentration of 1% w/v. An optimum pH of the hyaluronic acid sodium salt and de-ionized water solution is monitored and maintained. The methacrylic anhydride is added dropwise to the solution comprising hyaluronic acid sodium salt and de-ionized water to obtain a solution mixture. A pH of 8 is maintained for the solution mixture of hyaluronic acid sodium salt, de-ionized water and methacrylic anhydride. The solution mixture is incubated on ice for a predetermined time period. The pH is monitored at regular interval of time. The pH of the solution mixture is maintained at 8. The solution mixture is agitated for 24 hours in a cold room. A temperature of the cold room is maintained at 4° C. The solution mixture is dialyzed for two days in distilled water. The plurality of solutions are obtained from dialysis. The plurality of solutions obtained from dialysis are changed using 12-14 kDa molecular weight cut-off (MWCO) dialysis tubes. The plurality of solutions are lyophilized for one week to obtain methacrylated hyaluronic acid. The methacrylated hyaluronic acid is stored at −80° C.

According to one embodiment herein, the step of synthesizing metharylated gelatin (GelMA), comprises the following steps. The porcine skin type A gelatin is mixed in Dulbecco's phosphate-buffered saline (DPBS) to obtain a gelatin solution. The gelatin solution is incubated at 60° C. for dissolving the porcine skin type A gelatin in Dulbecco's phosphate-buffered saline (DPBS). The methacrylated anhydride is added dropwise in the gelatin solution to obtain an emulsion. The methacrylated anhydride has a concentration of 0.8 ml/g. The emulsion comprising gelatin and methacrylic anhydride is agitated at a temperature of 60° C. for a time period of 1 hour. The warm DPBS is added to the emulsion for inhibiting a reaction within the emulsion to obtain a mixture. The temperature of DPBS is 40° C. The concentration of DPBS is 2×. The mixture comprising gelatin, methacrylic anhydride and DPBS is dialyzed for 1 week in distilled water using MWCO dialysis tubes. A plurality of solutions are obtained from dialysis. The plurality of solution obtained after dialysis are frozen for a period of 1 week to obtain a white and porous foam of metharylated gelatin (GelMA). The foam of metharylated gelatin (GelMA) is incubated at a temperature of −80° C.

According to one embodiment herein, the step of synthesizing poly (glycerol sebacate)-poly(ε-caprolactone) (PGS-PCL) microfibrous scaffolds, comprises the following steps. A frame is fabricated. The frame comprises a copper wire covered with a non-adhesive tape with a glass slide on top. The poly (glycerol sebacate) and poly(ε-caprolactone) polymers in a predetermined ratio are dissolved in an anhydrous chloroform-ethanol solvent to obtain a solution. The ratio of poly (glycerol sebacate) and poly(ε-caprolactone) is 2:1. The solution comprising poly (glycerol sebacate)-poly(ε-caprolactone) polymers and anhydrous chloroform-ethanol solvent is subjected to electrospinning at 12.5 kV. A concentration of total polymer is 33% w/v. A distance of 10 cm is maintained between electrospinning needle and collector to obtain poly (glycerol sebacate)-poly(ε-caprolactone) (PGS-PCL) microfibrous scaffolds. The dimensions of the needle is 21 gauge. A flow rate of 2 ml/hour is maintained in the elelctrospinning machine. The poly (glycerol sebacate)-poly (ε-caprolactone) (PGS-PCL) microfibrous scaffolds are dried for 24 hours in a vacuum desiccator for removing residual solvents.

According to one embodiment herein, the step of synthesizing hydrogel (hydrogel precursor solution), comprises the following steps. The methacrylated gelatin (GelMA) and methacrylated hyaluronic acid (HAMA) are mixed with endothelial basal medium to obtain a solution. The photoinitiator is added in the solution for obtaining a mixture. The concentration of the photoinitiator is 0.1% v/w. The photoinitiator crosslinks the solution. The photoinitiator is 2-hydroxy-1-(4-(hydroxyethoxy)phenyl)-2-methyl-1-propanone. The mixture is exposed to UV light for a time period of 45 second at 2.6 mW/cm$^2$. A wavelength of UV light is 408 nm. A hydrogel or hydrogel precursor solution is obtained with an initial solution volume of 20 μl. The diameter of the hydrogel is 6 mm. The thickness of the hydrogel is 0.5 mm. The hydrogel or hydrogel precursor is used for the synthesis/fabrication of composite scaffolds. The step of fabricating composite scaffold comprising hydrogel and poly (glycerol sebacate)-poly(ε-caprolactone) (PGS-PCL) microfibrous scaffolds, comprises the following steps. The poly (glycerol sebacate)-poly(ε-caprolactone) (PGS-PCL) microfibrous scaffolds are arranged to obtain scaffolds of 6 mm diameter. The poly (glycerol sebacate)-poly(ε-caprolactone) (PGS-PCL) microfibrous scaffolds are arranged in sheets. The hydrogel is added in the poly (glycerol sebacate)-poly(ε-caprolactone) (PGS-PCL) microfibrous scaffolds. The amount of the hydrogel is 20 ml. The poly (glycerol sebacate)-poly(ε-caprolactone) (PGS-PCL) microfibrous scaffolds absorb the hydrogel. The poly (glycerol sebacate)-poly(ε-caprolactone) (PGS-PCL) microfibrous scaffolds and the hydrogel are exposed for crosslinking. The poly (glycerol sebacate)-poly(ε-caprolactone) (PGS-PCL) microfibrous scaffolds and the hydrogel are exposed to UV light for a time period of 45 second at 2.6 mW/cm2. The wavelength of UV light is 408 nm. The composite scaffold comprises elelctrospun poly(glycerol sebacate)-poly(ε-caprolactone) (PGS-PCL) microfibrous scaffold within a hybrid hydrogel comprising methacrylated hyaluronic acid and methacrylated gelatin.

According to one embodiment herein, the step of encapsulating fibroblast cells within the composite scaffold comprising hydrogel and poly (glycerol sebacate)-poly(ε-caprolactone) (PGS-PCL) microfibrous scaffolds and hydrogels, comprises the following steps. The fibroblast cells are cultured in a culture medium supplemented with 10% fetal bovine serum and 1% Penicillin-Streptomycin in predetermined atmospheric conditions. The predetermined atmospheric conditions comprises a temperature of 37° C. and carbon dioxide at a concentration of 5%. The fibroblast cells are cultured/grown on gelatin coated flasks. The fibroblast cells are passaged weekly. The fibroblast cells are trypsinized. The fibroblast cells are re-suspended in a hydrogel precursor solution at a predetermined concentration. The hydrogel precursor solution comprises methacrylated gelatin (GelMA) and methacrylated hyaluronic acid (HAMA) and photoinitiator. The concentration of fibroblast cells suspended is 6×10$^6$ cells/ml. The composite scaffolds and the hydrogel precursor with fibroblast cells are exposed to UV light for a time period of 45 second at 2.6 mW/cm2. The wavelength of UV light is 408 nm. The composite scaffolds and hydrogel precursor solution with fibroblast cells are incubated in a culture medium for a time period of 21 days in predetermined conditions. The composite scaffold comprises hydrogel and poly (glycerol sebacate)-poly(ε-caprolactone) (PGS-PCL) microfibrous scaffolds. The culture medium is changed every 30 minutes for first two hours. The cultured medium is changed every 30 minutes for removing photoinitiator.

According to one embodiment herein, the step of seeding fibroblast cells on composite scaffold and PGS-PCL scaffold, comprises the following steps. The composite scaffolds and PGS-PCL scaffolds are sterilized by immersion in 70% ethanol for 2 hours. The composite scaffold comprises poly (glycerol sebacate)-poly(ε-caprolactone) (PGS-PCL) microfibrous scaffolds and hydrogels. The sterilized composite scaffolds and PGS-PCL scaffolds are exposed to UV radiation for a predetermined time. The sterilized composite scaffolds and PGS-PCL scaffolds are washed with DPBS medium. The fibroblast cells are selected at a concentration of $2 \times 10^4$ cells/scaffold. A predetermined volume of fibroblast cells suspension is added on the composite scaffolds and PGS-PCL scaffolds placed in a 48-well culture plate. The predetermined volume of fibroblast cells is 20μl. The 48 well plate comprising the composite scaffolds and PGS-PCL scaffolds with fibroblast cell suspension is incubated for a time period of 1 hour. The fibroblast cells is attached to the composite scaffolds and PGS-PCL scaffolds in incubation. The culture medium is changed every day.

According to one embodiment herein, the step of soaking the poly (glycerol sebacate)-poly(ε-caprolactone) (PGS-PCL) microfibrous scaffolds and the poly(ε-caprolactone) (PCL) fibres in the hydrogel precursor solution, comprises the following steps. The PGS-PCL scaffolds and the PCL scaffolds are synthesized. The size of the PGS-PCL scaffolds and PCL scaffolds is 6 mm diameter. The PCL scaffolds are negative control. The 20 μl of the hydrogel solution is added on the PGS-PCL scaffolds and the PCL scaffolds. The PGS-PCL fibres and the PCL fibres are soaked with hydrogel for a predetermined amount of time. The hydrogel with PGS-PCL fibres and the PCL fibres is imaged to analyse the imbibition of hydrogel in the PGS-PCL fibres and PCL fibres. The poly (glycerol sebacate) (PGL) component facilitates the penetration and imbibition of the hydrogel in the PGS-PCL microfibers. The PCL microfiber illustrate less absorption and imbibition of hydrogel when compared to the PGS-PCL microfibers. The imaging illustrates that the hydrogel penetrates into the PGS-PCL microfibers.

According to one embodiment herein, the analysis of a plurality of physico-chemical characteristics of the composite scaffold, PGS-PCL scaffold and hydrogel scaffold illustrate that the composite scaffold comprising hydrogel and poly (glycerol sebacate)-poly(ε-caprolactone) (PGS-PCL) microfibrous scaffolds has hydrophilic property. The hydrophilic property is imparted by the PGS-PCL component. The swelling ratio in the composite scaffold increased (p<0.05) after UV exposure.

According to one embodiment herein, the analysis of fibroblast cell viability, fibroblast cell attachment, fibroblast cell spreading, fibroblast cell proliferation and fibroblast cell metabolism in the composite scaffolds, PGS-PCL scaffolds and hydrogels illustrate that the fibroblast cells are spread in the composite hydrogel unevenly. The fibroblast cells are spread evenly in the hydrogel scaffold. The fibroblast cells are spread on the surface of PGS-PCL scaffold. The cell viability of fibroblast cell is above 90% in hydrogel, PGS-PCL scaffold and composite scaffolds. The fibroblast cells illustrate a high metabolic activity in composite scaffold when compared with the fibroblast cells present in PGS-PCL scaffold and hydrogel scaffold.

According to one embodiment herein, the hydrogel component of the composite scaffold provides an extracellular mimicking environment for fibroblast cells. The hydrogel component provides an ability of fibroblast cell delivery to an affected skin tissue. The PGS-PCL component of the composite scaffold facilitate a distribution of the fibroblast cells within the hydrogel component. The PGS-PCL component provides mechanical support to the composite scaffold.

FIG. 1 illustrates a flowchart indicating an overall method of fabricating and analyzing scaffolds for skin tissue regeneration, according to one embodiment herein. Methacrylated hyaluronic acid (HA) and methacrylated gelatin are synthesized (101). PGS-PCL microfibrous scaffold is synthesized (102). The hydrogel (hydrogel precursor solution) is synthesized from GelMA/HAMA (103). The composite scaffold comprising hydrogel and PGS-PCL microfibrous scaffolds are synthesized (104). The fibroblast cells are cultured in predetermined conditions (105). The fibroblast cells are encapsulated within the hydrogels (GelMA/HAMA) and in the composite scaffolds comprising hydrogel and the PGS-PCL microfibrous scaffolds separately (106). The fibroblast cells are seeded on composite scaffold and the PGS-PCL scaffold separately (107). The PGS-PCL microfibrous scaffolds and the PCL fibers are soaked in the hydrogel precursor solution (108). A plurality of physico-chemical characteristics of the composite scaffolds, PGS-PCL microfibrous scaffolds is analyzed. The physico-chemical properties are mechanical properties, swelling ratio, enzymatic degradation and structural analysis by scanning electron microscope imaging (109). The cell viability, fibroblast cell attachment, fibroblast cell spreading, fibroblast cell proliferation and fibroblast cell metabolism are analyzed in composite scaffolds, PGS-PCL scaffolds and hydrogels (110).

Experimnet—1 Synthesis of Methacrylated Hyaluronic Acid (HA) and Methacrylated Gelatin:

Hyaluronic acid (HA) sodium salt is dissolved to a final concentration of 1% w/v in deionized water (dI H2O). The pH of the solution is monitored during this process. Methacrylic anhydride is added dropwise (2 ml/200 ml) while maintaining the pH at 8.0. The solution is put on ice for several hours and is monitored every 15 min for checking the pH to be maintained at 8. The solution comprising hyaluronic acid and methacrylic anhydride is agitated overnight in a cold room (4° C.) and is dialyzed for two days in distilled water (dI H2O) with multiple solution changes using 12-14 kDa molecular weight cut-off (MWCO) dialysis tubes. The solutions are lyophilized for one week, and the final product is stored at −80° C. for future use.

Porcine skin type A gelatin is methacrylated by a standard predetermined protocol. 10% (w/v) gelatin is mixed in Dulbecco's phosphate-buffered saline and incubated at 60° C. until completely dissolved. Methacrylic anhydride (0.8 ml/g) (8 ml) is added dropwise at a rate of 0.5 ml/min into the gelatin (10 g) solution. The emulsion comprising gelatin and methacrylic anhydride is agitated at 60° C. for 1 h. Warm 2× DPBS (40° C.) is added to the solution to prevent any further reaction. The solution is dialyzed for one week in distilled water using MWCO dialysis tubes with several solution changes. The solution is freeze-dried for one week then resulted in white, porous foam that is kept at −80° C. to be used in the future.

Experimnet —2 PGS-PCL Microfibrous Scaffold Formation:

Poly (glycerol sebacate)-poly(ε-caprolactone) (PGS-PCL) microfibrous scaffolds are prepared by using a standard electrospinning setup. The copper wire is covered with a non-adhesive special tape with a glass slide on top, which acts as a framework. PGS and PCL are dissolved at a 2:1 ratio in anhydrous chloroform-ethanol solvent (9:1 v/v) and are electrospun at 12.5 kV. The total polymer is 33%. Pure PCL scaffolds are electrospun using 16% w/v polymer solution because it is difficult to electrospin the highly viscous 33% w/v PCL solution. The fibers are fabricated, while the distance between the needle (21-gauge needle) and the collector is kept at 18 cm, at a flow rate of 2 ml/h. Each sample is fabricated in 20 min. The scaffolds obtained are dried overnight in a vacuum desiccator and all residual solvents are removed.

Experimnet —3 Hydrogel Synthesis:

A hydrogel precursor solution is mixed with medium. The solution is crosslinked by adding the photoinitiator (PI) 2-hydroxy-1-(4-(hydroxyethoxy) phenyl)-2-methyl-1-propanone to a final concentration of 0.1% (v/w) and exposing it to UV light ($\lambda$=408 nm) for 45 second at 2.6 mW/cm2. The resulting hydrogel (20 μl initial solution volume, 6 mm diameter, 0.5 mm thick) is used as a control and is also used for making the composite scaffolds.

Experimnet —4 Fabrication of Composite Hydrogel/Microfibrous PGS-PCL Scaffolds:

PGS-PCL bulk sheets are used to create 6-mm diameter scaffolds. The PGS-PCL scaffolds are put into contact with the precursor hydrogel solution. Once the scaffold fully absorbs the solution, the resulting composite is crosslinked using UV light ($\lambda$=408 nm, 2.6 mW/cm2, 45 seconds). The composite scaffold comprises hydrogel and poly (glycerol sebacate)-poly(ε-caprolactone) (PGS-PCL) microfibrous scaffolds.

Experimnet —5 Hydrogel Precursor Solution Soaking Into PGS-PCL and PCL Fibers:

Scaffolds (6-mm diameter) are created from both PGS-PCL and PCL-only (negative control) and are then filled with 20 ml hydrogel solution by putting the solution volume on top of each scaffold. Soaking of the drop into the PGS-PCL actual fibers is imaged as both sequential series (1 second intervals) and in video format. PCL-only scaffolds are used as the negative control.

Experimnet —6 Physical Characterization of the Scaffold:

Mechanical properties—For mechanical characterization of the samples, a uniaxial elongation test is performed on at least six samples using an Instron 544 and a 10-N load cell. Electrospun (ES) meshes are cut into rectangular shapes (5 mm×20 mm). In order to prepare composite samples for mechanical testing, PGS-PCL scaffolds are cut and placed in the molds. Molds are filled by pipetting 20 ml hydrogel solution on top of each ES scaffold. Composites are formed by exposing the mold to the UV light ($\lambda$=408 nm, 2.6 mW/cm2, 45 s) and then detached from the mold. The composite samples are tested while still wet. Sandpapers are attached to the top and bottom of the composite samples to prevent them from slipping before failure. The samples are loaded at a rate of 7 mm/min. The elastic modulus (EM) is measured using the Young's modulus based on the linear portion of the stress-strain curve. The ultimate tensile strength (UTS) is calculated using the maximum strength obtained from the stress-strain curve.

Swelling ratio—Hydrogels and composite scaffolds are prepared as disclosed in methods above. The composite scaffold comprises hydrogel and poly (glycerol sebacate)-poly(ε-caprolactone) (PGS-PCL) microfibrous scaffolds. The swelling behavior of the hydrogel and the composite is analyzed after equilibrating the samples in PBS at 37° C. for 24 h. The excess liquid is removed from the completely swollen samples before weighing (swollen weight). The samples are then freeze-dried and weighed again (dry weight) (n≥6). The swelling ratio is measured by dividing the samples' swollen weight by the dry weight. For the composites, the dry weight of the PGS-PCL scaffold is measured and subtracted during the calculation of swelling ratio.

In vitro hydrogel and the composite scaffold's enzymatic degradation—The hydrogel samples (n≥6) are crosslinked as disclosed in the methods above. The composite scaffold comprises hydrogel and poly (glycerol sebacate)-poly(ε-caprolactone) (PGS-PCL) microfibrous scaffolds are fabricated as disclosed above. Collagenase (1 U/ml) from *Clostridium histolyticum* and hyaluronidase type 1-S (100 U/ml) from bovine testes solutions are prepared in PBS from stock solutions. The hydrogel samples are incubated in collagenase (1 U/mg; n≥6), hyaluronidase (100 U/ml; n≥6), or PBS (n≥6) at 37° C. for 24 h. The samples were weighed before and after adding the enzymatic solution. After incubation, the samples are washed, lyophilized, and weighed again. The degradation was calculated by determining the decrease in mass. The samples were stored at 37° C. for 48 h before fixing them in 2.5% glutaraldehyde and observing the hydrolytic degradation via scanning electron microscopy (SEM).

Scanning Electron Microscopy (SEM)—The SEM images are taken with the use of the field emission scanning electron microscope to characterize the pore size of the scaffold and the fiber morphology. Images are taken from both surface and internal cross-sections of the hydrogel-only, the composites scaffold, and the PGS-PCL only scaffold with and without cells (Day 0 and Day 21). The composite scaffold comprises hydrogel and poly (glycerol sebacate)-poly(ε-caprolactone) (PGS-PCL) microfibrous scaffolds. The samples (hydrogel, composite scaffold and PGS-PCL only scaffold with and without cells) are fixed in 2.5% glutaraldehyde and are frozen using liquid nitrogen. The samples are stored at −80° C. The samples are lyophilized before sputter coating them with an iron coater using palladium and platinum. The SEM is equilibrated at 40 mA for 40 seconds prior to taking the images.

Experimnet —7 Fibroblast Cells Culture:

Fibroblast Cell Culture—Fibroblast cells passage number 3 and 4 are maintained in media culture supplemented with 10% fetal bovine serum (FBS) and 1% Penicillin-Streptomycin at 37° C. and 5% $CO_2$. The cells are cultured on gelatin coated flasks and are passaged weekly with media changed every other day.

Encapsulation of Fibroblasts Within Hydrogels (GelMa/HAMA) And Composite Scaffolds—Fibroblasts are trypsinized and re-suspended in the hydrogel precursor solution comprising 0.1% (w/v) photo initiator at a concentration of $6\times10^6$ cells/ml. The hydrogel and composite scaffolds are fabricated as illustrated in above disclosed methods. The composite scaffold comprises hydrogel and poly (glycerol sebacate)-poly(ε-caprolactone) (PGS-PCL) microfibrous scaffolds. The scaffolds and hydrogel precursor solution with cells are exposed to 2.6 mW/cm$^2$ UV light (408 nm) for 45 seconds and are then incubated in medium under standard culture conditions for 21 days. The medium is changed every 30 minutes for the first two hours to remove the remaining photoinitiator. The medium is then changed every other day.

Seeding Fibroblasts On PGS-PCL Scaffolds And Composite Scaffolds—PGS-PCL scaffolds and composite scaffolds are sterilized prior to seeding with the fibroblast cells by immersing them in 70% ethanol for 2 hours. The composite scaffold comprises hydrogel and poly (glycerol sebacate)-poly(ε-caprolactone) (PGS-PCL) microfibrous scaffolds. It is followed by UV exposure and washing with DPBS. Then the cells are selected onto scaffolds (0.6 cm×0.6 cm) at a concentration of $2 \times 10^4$ cells/scaffold. Cells are seeded onto scaffolds by adding 20 µl of cell suspension to scaffolds in 48-well plates and incubating them for 1 hour to allow the cells to attach. The medium is changed every other day.

Experimnet —8 Analyzing Fibroblast Cell Viability, Fibroblast Cell Attachment, Fibroblast Cell Spreading, Fibroblast Cell Proliferation and Fibroblast Metabolism in Composite Scaffolds and PGS-PCL Scaffolds and Hydrogels:

CELL VIABILITY—The cell viability within the scaffolds is quantified with the use of a live-dead assay per manufacturer's protocol. The viability of the cells is determined on $1^{st}$ day (24 hours after cell seeding/encapsulation) and $21^{st}$ day of culture for each type of sample. The samples are imaged using a Fluorescent microscope. Image J software is used to assess the percent viability.

CELL ATTACHMENT AND CELL SPREADING—Cell adhesion analysis is performed by encapsulating $6 \times 10^6$ cells/ml fibroblasts with each scaffold disclosed in above method. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds. The scaffolds with fibroblast cells are incubated for 21 days. The media of the samples is changed every other day. After 21 day, the scaffolds are fixed and stained by rhodamine-phalloidin and 4, 6-diamino-2-phenylindole. The degree of cell attachment and spreading is assessed by FE-SEM.

CELL METABOLISM—The metabolic activity of cells on each scaffold or hydrogel at 1 and 21 days of culture is assessed with the use of the Alamar Blue (AB) assay according to manufacturer's protocol. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds. The cells are seeded onto scaffolds or are encapsulated within plain hydrogels or composite scaffolds (n=3/group). The cell-seeded scaffolds are then transferred to new wells to avoid counting cells that had adhered to the plate surface during seeding. One well, which comprises only medium, is used to measure background signal, while two cell-free scaffolds/hydrogels are used as the negative controls. The control scaffolds had the same no-cell condition for each type, as the baseline readings are not the same and this was taken into account in calculations. AB is dissolved in 10% v/v medium and then added to each well. The samples are kept in an incubator in AB for 2 h at 37° C. Subsequently solution from each well is transferred to wells in a 96-well plate (100 µl, n=3/group) and the fluorescence is measured (excitation: 540 nm, emission: 590 nm). The 21-day measurements are normalized to the corresponding measurements from day 1.

Experimnet —9 Statistical Analysis:

Statistical Analysis is performed using SPSS version 15.0 (SPSS Inc., Chicago, USA). Data is illustrated as the mean±standard deviation. Kolmogorov-Smirnov test is performed to determine if the factors are normally distributed. Three groups of PGS-PCL fiber, hydrogel, and composite scaffold are compared by one way ANOVA. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds. This is followed by Tukey HSD test. Independent T test is performed to compression of mean of composite scaffold, hydrogel and PGS-PCL groups. A p value≤0.05 is considered statistically significant. Data are shown as the mean±standard deviation. The composite scaffold comprises hydrogel and poly (glycerol sebacate)-poly (ε-caprolactone) (PGS-PCL) microfibrous scaffolds Result —1 Physical Characterization of the Composite Scaffolds:

The presence of poly(glycerol sebacate) (PGS) renders PGS-PCL microfibrous scaffolds hydrophilic property. The hydrophilic property of the poly (glycerol sebacate)-poly(ε-caprolactone) (PGS-PCL) is combined with the addition of an extracellular matrix environment within and around the microfibers by adding hydrogel. The scanning electron microscope (SEM) image of the composites illustrate that the composite scaffold fibers are completely encapsulated within a layer of hydrogel.

Figure 2:
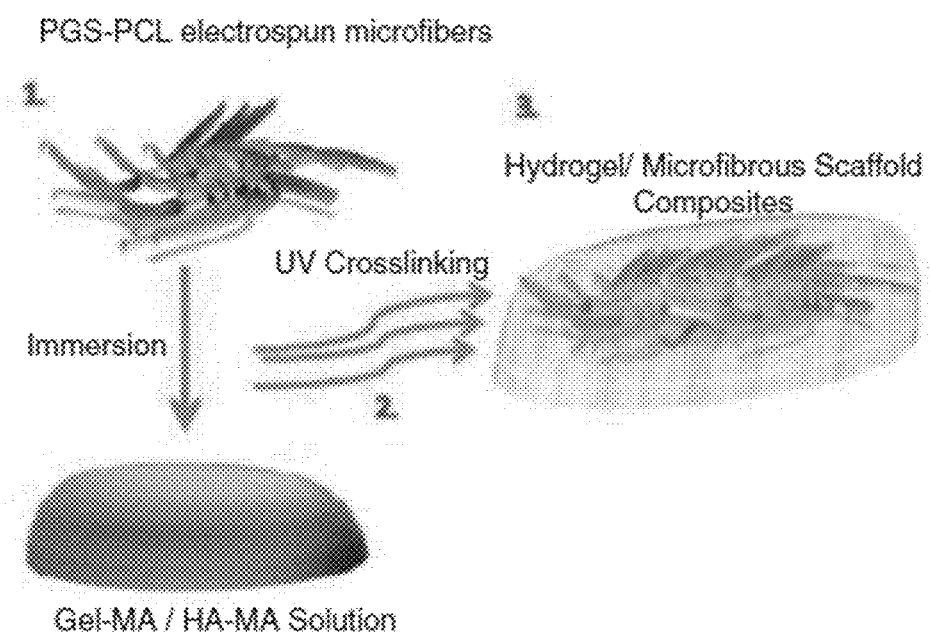
FIG. 2 illustrate a schematic flow diagram illustrating the fabrication of fiber reinforced hydrogel, according to one embodiment herein.

FIG. 2 illustrate a schematic flow diagram illustrating the fabrication of fiber reinforced hydrogel, according to one embodiment herein. FIG. 2 illustrates that electrospun fibers are immersed/embedded inside the hydrogel precursor solution (to which cells can be added). The crosslinking of the fibers is performed by UV light exposure to form a cell-laden hydrogel with electrospun fibers for reinforcement. The presence of poly(glycerol sebacate) (PGS) facilitates rapid immersion of the fibers into the hydrophilic gel precursor.

Figure 3:
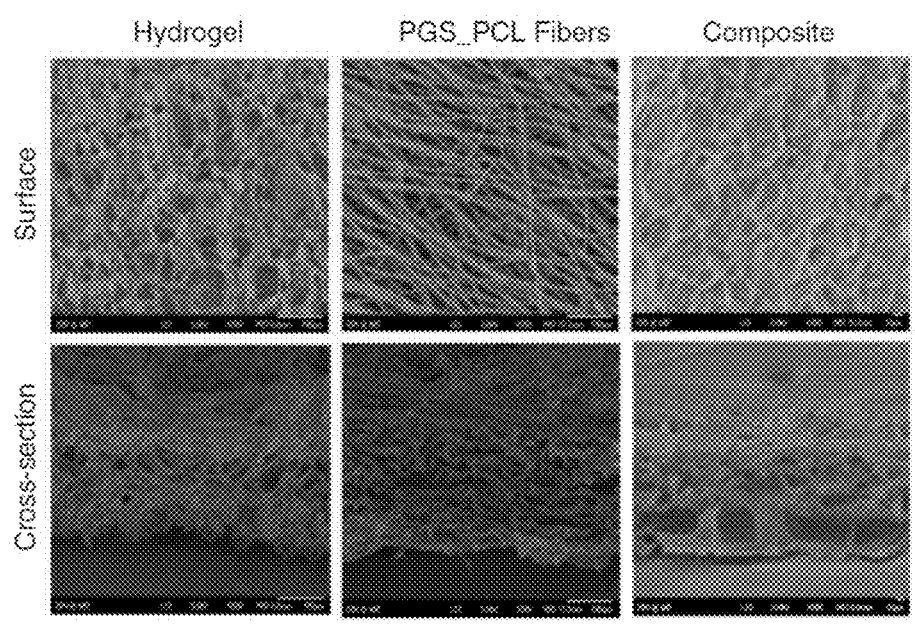
FIG. 3 is scanning electron microscope (SEM) image of hydrogel, poly (glycerol sebacate)-poly(ε-caprolactone) (PGS-PCL) fiber and composite (composite comprising both hydrogel and PGS-PCL fiber), according to one embodiment herein.

FIG. 3 is scanning electron microscope (SEM) image of hydrogel, poly(glycerol sebacate)-poly(εcaprolactone) (PGS-PCL) fiber and composite scaffold (composite comprising both hydrogel and PGS-PCL fiber), according to one embodiment herein. FIG. 3 illustrates the integration of the hydrogel with the electrospun fiber. The SEM images of the composite illustrate that the scaffold fibers are encapsulated within a layer of hydrogel. The PGS component of the microfibers is necessary to facilitate the complete interface because the GelMA/HAMA gel solution is unable to penetrate fibers comprising only PCL.

According to one embodiment herein, the gel solution is absorbed quickly when the scaffold is immersed in the gel solution. The composite structures are synthesized using immersion method. The advantage of the method/protocol followed is because of the PGS-PCL microfibers, which help or promote imbibition of hydrogel precursor solution in the composite scaffold. The composite scaffold is also produced after electrospinning and the cells are directly encapsulated within the composite during hydrogel crosslinking step.

According to one embodiment herein, the hydrogel/scaffold composite remodel the structure without compromising the mechanical properties. The gel component is enzymatically degraded in vivo during the remodeling process, which is a necessary step in the tissue healing process. The enzymatic degradation of gelatin and hyaluronic acid happen at different rates, the stability of the composite under enzymatic conditions is analyzed. The composite scaffolds are incubated with extracellular matrix (ECM)-degrading enzymes to observe the changes in the network of cross-linked methacrylated gelatin/methacrylated hyaluronic acid (GelMA/HAMA). The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds.

According to one embodiment herein, the gel component is completely degraded (92.0±8.0%) after 24 hours of collagenase treatment at 37° C. This illustrates that the enzymatic degradation of GelMA partially removes the hyaluronic acid. The composite scaffolds incubated with hyaluronidase illustrate similar results, which illustrates in 50% weight loss (45.94±8.1%).

According to one embodiment herein, the temporal and spatial degradation profile of the hydrogel affects the kinetics of the remodeling process in vivo. This illustrates the advantage of using a fibrillar scaffold/hydrogel composite.

Figure 4:
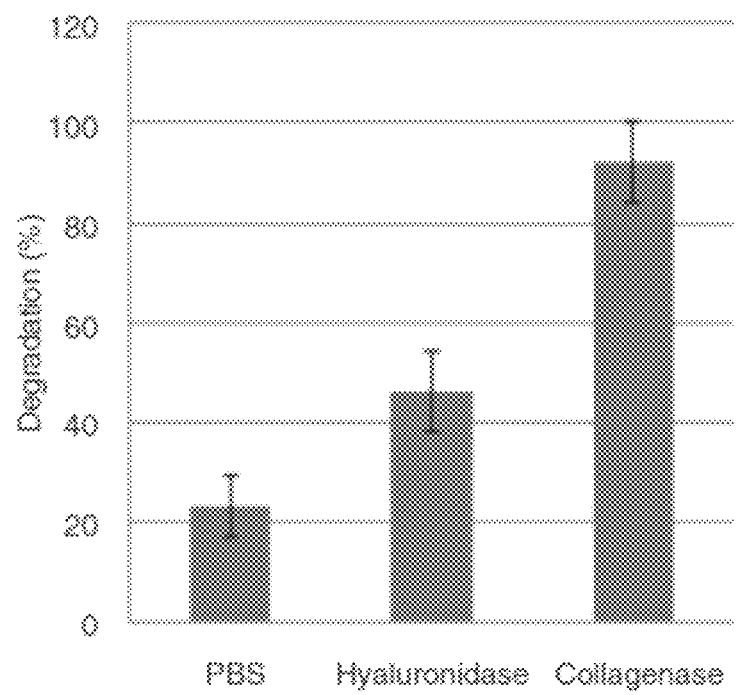
FIG. 4 is a graph illustrating the dry mass measurements of the composite scaffold samples incubated in phosphate-buffered saline (PBS), hyaluronidase and collagenase, according to one embodiment herein.

FIG. 4 is a graph illustrating the dry mass measurements of the composite scaffold samples incubated in phosphate-buffered saline (PBS), hyaluronidase and collagenase, according to one embodiment herein. The hydrolytic and enzymatic degradation profile of the composite scaffold incubated in PBS, collagenase and hyaluronidase for 24 hours. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds.

Figure 5:
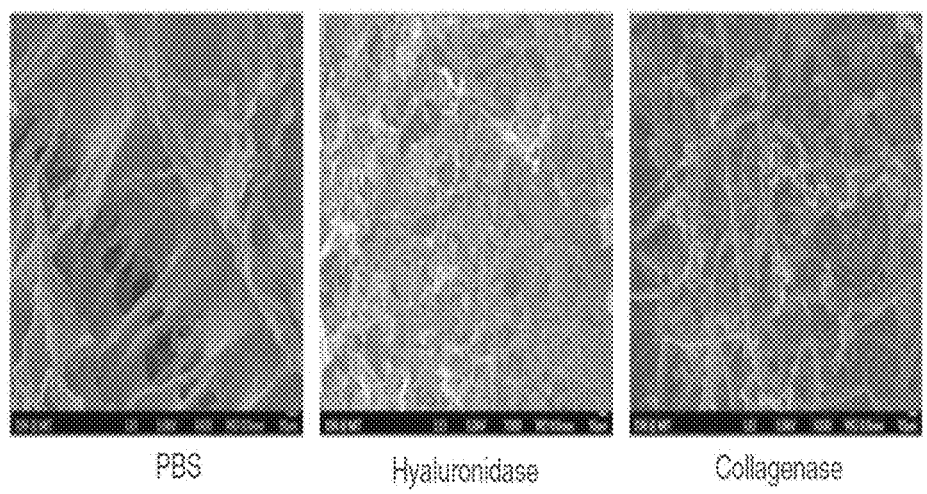
FIG. 5 is the scanning electron microscope (SEM) image illustrating hydrolytic and enzymatic degradation profile of the composite scaffold incubated in phosphate buffered saline, hyaluronidase and collagenase, according to one embodiment herein.

FIG. 5 is the scanning electron microscope (SEM) image illustrating hydrolytic and enzymatic degradation profile of the composite scaffold incubated in phosphate buffered saline, hyaluronidase and collagenase, according to one embodiment herein. The composite scaffold is incubated in PBS, collagenase and hyaluronidase for 24 hours. FIG. 5 illustrate that the maximum degradation of the composite scaffold is observed after incubating the composite scaffold in collagenase. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds.

According to one embodiment herein, the gel component of the composite scaffold is comparatively intact after treating/incubating composite scaffold with hyaluronidase. The treating/incubating composite scaffold with phosphate buffer saline (PBS) removes only a small amount of the gel via surface degradation, leaving the fiber component completely embedded within the gel structure.

According to one embodiment herein, the swelling ratio of the hydrogel component with and without poly(glycerol sebacate)-poly(ε-caprolactone) (PGS-PCL) scaffold is determined to evaluate the effect of the microfibrillar mesh on the degree of hydrogel crosslinking.

Figure 6:
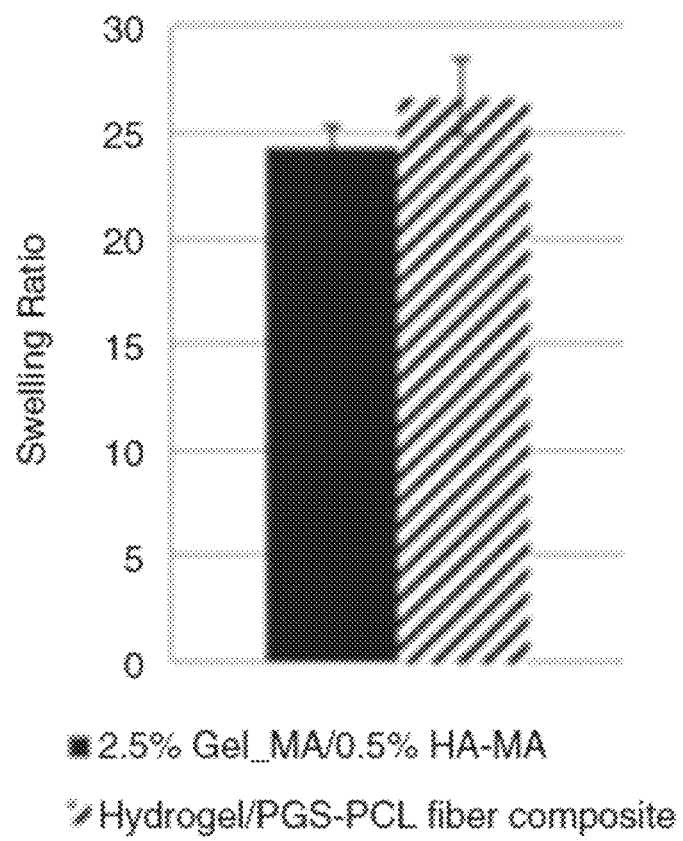
FIG. 6 is a graph illustrating the swelling ratio of the composite scaffold compared with hydrogel (n=6, p<0.05), according to one embodiment herein.

FIG. 6 is a graph illustrating the swelling ratio of the composite scaffold compared with hydrogel (n=6, p<0.05), according to one embodiment herein. The swelling ratio of the hydrogel component with and without the PGS-PCL scaffold is determined to evaluate the effect of the microfibrillar mesh on the degree of hydrogel crosslinking. FIG. 6 illustrate the swelling ratio of the composite scaffold samples increased (p<0.05), caused by attenuated UV exposure, creating a low level of crosslinking in the areas beneath the fiber layer. The composite scaffold comprises hydrogel and poly (glycerol sebacate)-poly(ε-caprolactone) (PGS-PCL) microfibrous scaffolds.

According to one embodiment herein, the native skin experience significant mechanical force, therefore the mechanical properties of skin replacement must withstand the same force. The composite scaffold mimics the structure of skin, recapitulating the collagenous layers via the fibrous PGS-PCL scaffold which provides mechanical strength while providing a 3D glycosaminoglycan rich extracellular matrix micro-environment. The microenvironment is remodeled by the cells in order to achieve a heterogeneous phenotype. The base of the scaffold is microfibrous poly (glycerol sebacate)-poly(ε-caprolactone) PGS-PCL scaffold. The methacrylated gelatin (GelMA) and methacrylated hyaluronic acid (HAMA) is added to overcome the porosity issue and allows the cells to penetrate inside the scaffold structure.

Figure 7A:
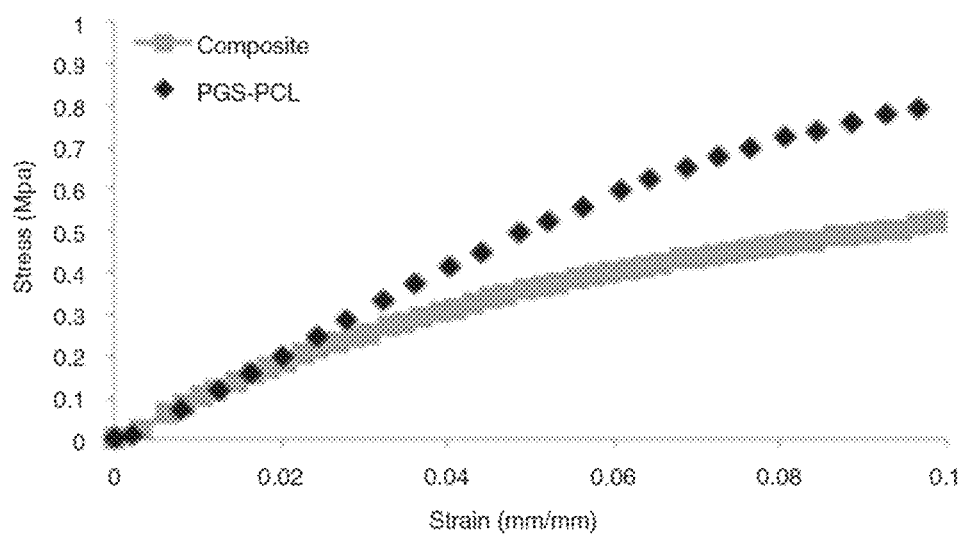
FIG. 7A-7C are graphs together illustrate the tensile mechanical properties of the composite scaffold, according to one embodiment herein.
Figure 7B:
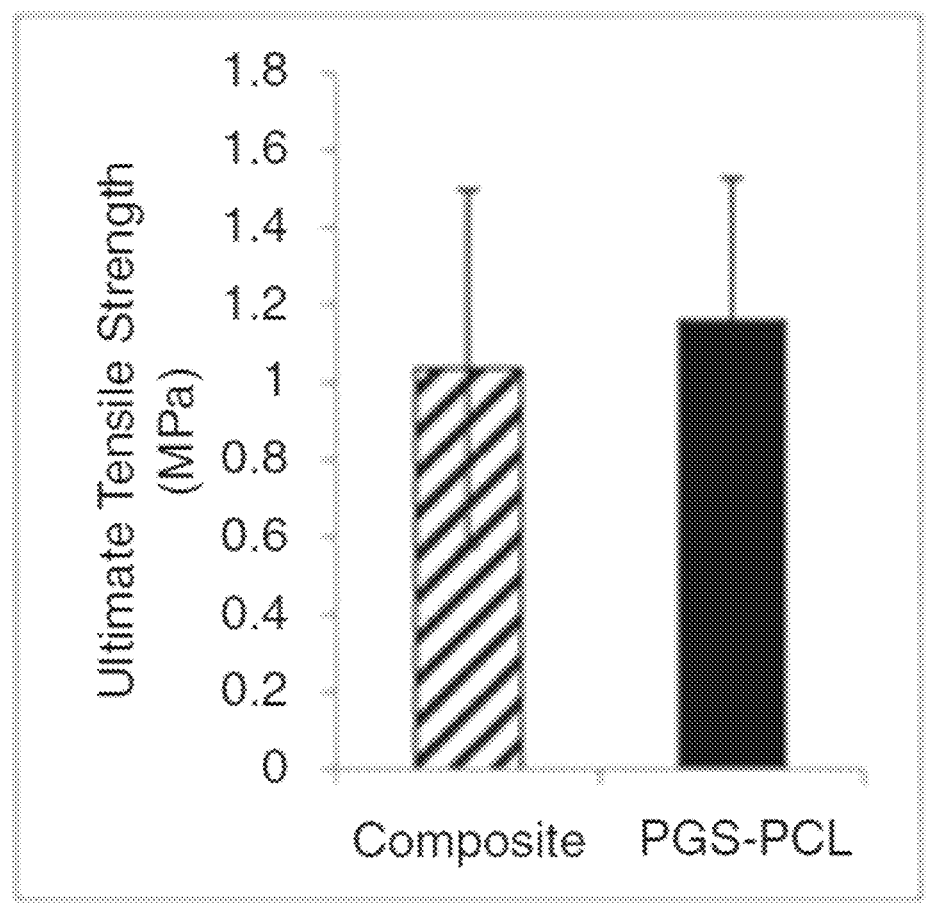
Figure 7C:
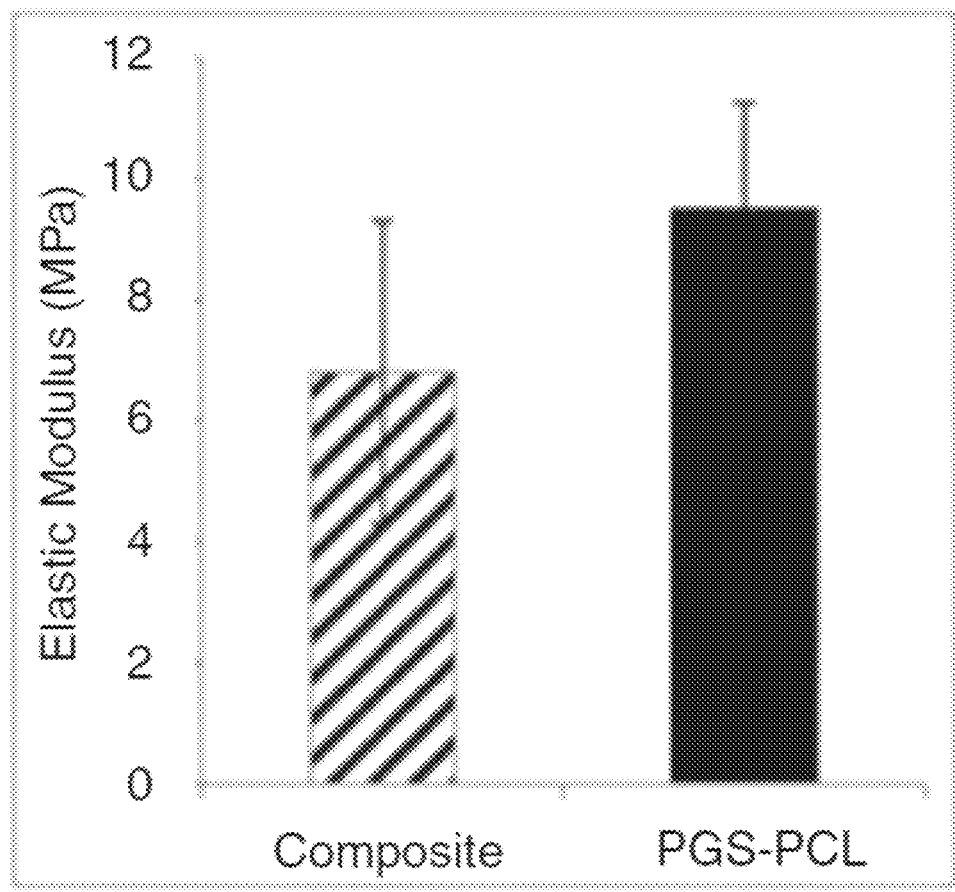

FIG. 7A-7C are graphs together illustrate the tensile mechanical properties of the composite scaffold, according to one embodiment herein. The tensile mechanical properties of the composites are compared to fibers (n=6). The composite scaffold has similar tensile mechanical properties to the fibers alone (p>0.05). The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds. FIG. 7A is a graph illustrating the stress in composite scaffold and PGS-PCL scaffolds. FIG. 7B is a graph illustrating the ultimate tensile stress in scaffold composite scaffold and PGS-PCL scaffolds. FIG. 7C is a graph illustrating the elastic modulus in composite scaffold and PGS-PCL scaffolds. The stiffness in PGS-PCL and ultimate tensile stress are in order of MPa. Hence adding GelMa and HAMA with much lower mechanical stiffness does not affect the overall mechanical properties of the composite, when compared to PGS-PCL scaffolds. The fibers expand and specifically deform up to 600%. Addition of GelMA-HAMA to PGS-PCL results in a composite that preserves the mechanical characteristics of PGS-PCL scaffolds which mimics the native skin. The addition of hydrogel component to PGS-PCL scaffolds did not significantly change the mechanical properties including the elastic modulus and the ultimate tensile strength.

According to one embodiment herein, the hydrogel component provides an environment to encapsulate cells in 3D environment without significantly (p>0.05) reducing the mechanical properties of the PGS-PCL structure. The fibrous components provide the mechanical properties to the composite scaffold.

Result —2 Encapsulating Fibroblast in Hydrogels and Composite Scaffolds:

According to one embodiment herein, the composite scaffolds incorporate a cross-linked glycosaminoglycan component. The glycosaminoglycan forms crosslinks with the other extracellular matrix (ECM), gelatin. Hence the fiber reinforced hydrogel scaffold does not leach out during long fibroblast cell culture period.

According to one embodiment herein, after encapsulation of fibroblast cells in either hydrogels alone, or the composite scaffold comprising hydrogel and poly(glycerol sebacate)-poly(ε-caprolactone) (PGS-PCL) scaffold [fiber reinforced hydrogel scaffold], illustrate homogeneous distribution. The fibroblast cell maintain viability in the hydrogels alone or the fiber reinforced hydrogel. The cellular distribution is uniform in the hydrogels, whereas the cells in the fiber reinforced hydrogel are distributed more unevenly.

Figure 8:
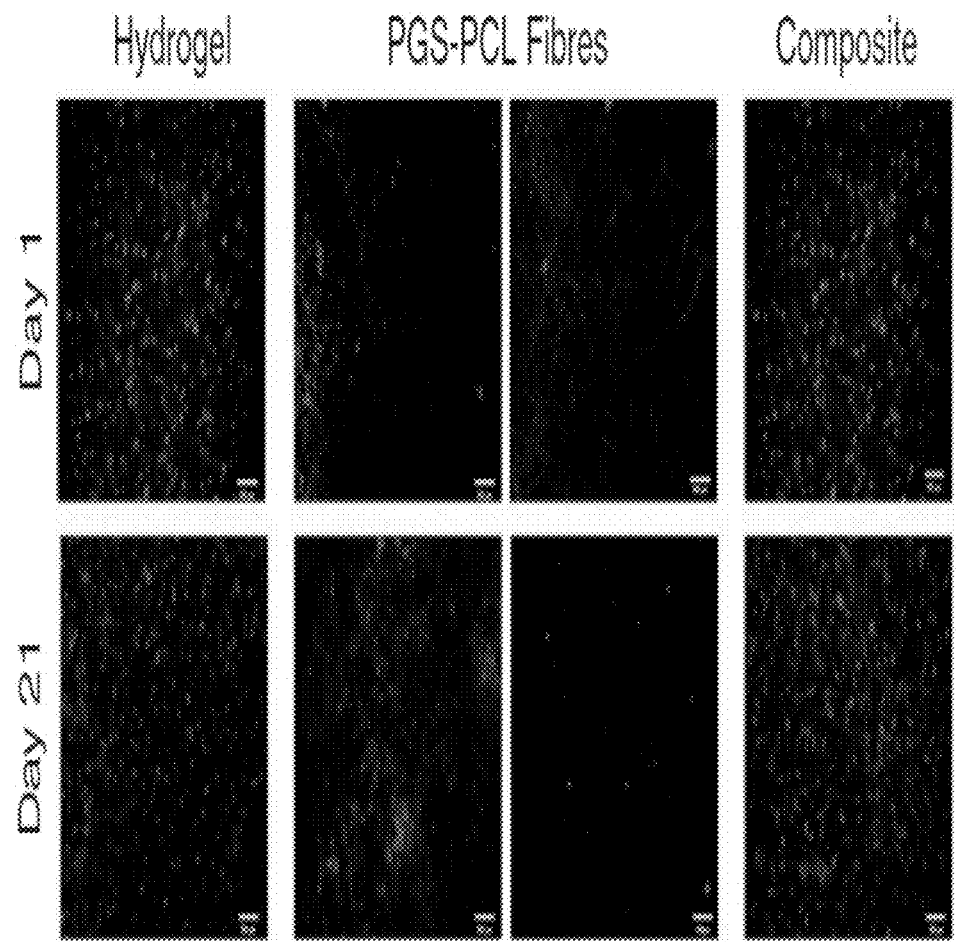
FIG. 8 is a photograph illustrating the viability of the encapsulated or seeded fibroblast cells by live/dead staining of the fibroblast cells, according to one embodiment herein.

FIG. 8 is a photograph illustrating the viability of the encapsulated or seeded fibroblast cells by live/dead staining of the fibroblast cells, according to one embodiment herein. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds. FIG. 8 illustrate the observations of the day 1 and day 21 of the viability of the fibroblast cells. The fibroblast cell distribution is uniform in the hydrogels, while the cells within the composite scaffolds are distributed more unevenly. The cells initially assumed a rounded shape but then began to spread over time. By day 21, the cells spread fully in both the hydrogel and composite structures. The bare PGS-PCL scaffold has cell spreading predominantly on its surface because the dense structure of the electrospun fibers temporarily limits cellular infiltration.

Figure 9:
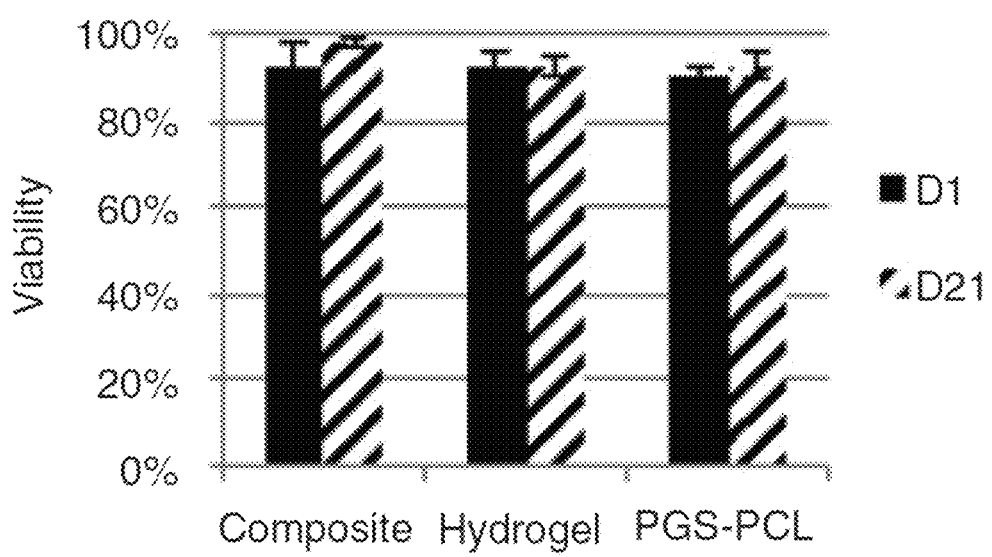
FIG. 9 is a graph illustrating quantification of the live/dead fibroblast cells in composite scaffold, according to one embodiment herein.

FIG. 9 is a graph illustrating quantification of the live/dead fibroblast cells in composite scaffold, according to one embodiment herein. The quantification of the live or dead fibroblast is analyzed by Image J software (n=3). The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds. After 21 days of fibroblast cell culture along with hydrogel scaffold, PGS-PCL scaffold and composite scaffold illustrate more number of cells around the fibrillar component of the scaffold. The number of cells towards fibrillar component is caused by migration of cells towards stiffer substrates.

Figure 10:
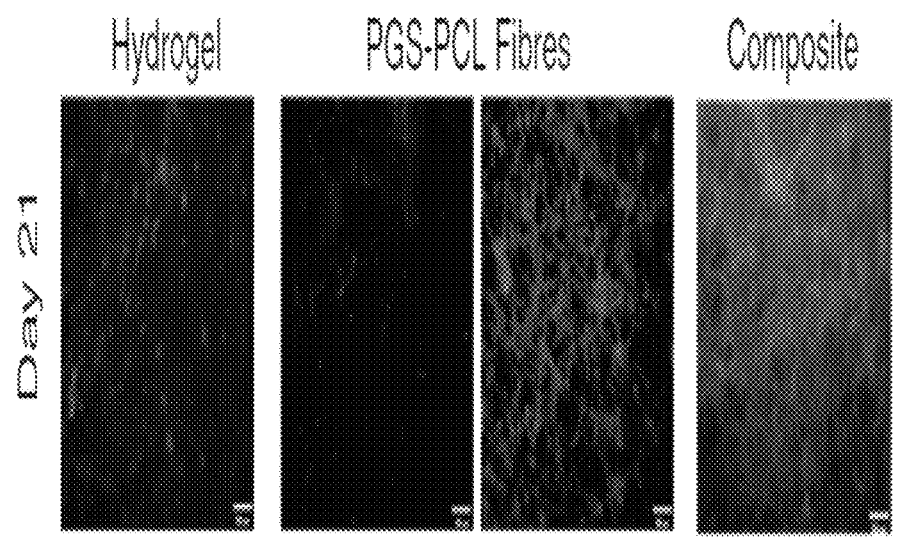
FIG. 10 is a photograph illustrating the results of cell viability analysis by DAPI/phalloidin staining on day 21, according to one embodiment herein.

FIG. 10 is a photograph illustrating the results of cell viability analysis by DAPI/phalloidin staining on day 21, according to one embodiment herein. The initial encapsulation process maintained a high level of cell viability (≥90%). At $21^{st}$ day the viability of fibroblasts is above 90% for all the three scaffolds i.e. hydrogel scaffold, PGS-PCL scaffold and composite scaffold. There is a significant increase in the cell number. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds.

Figure 11:
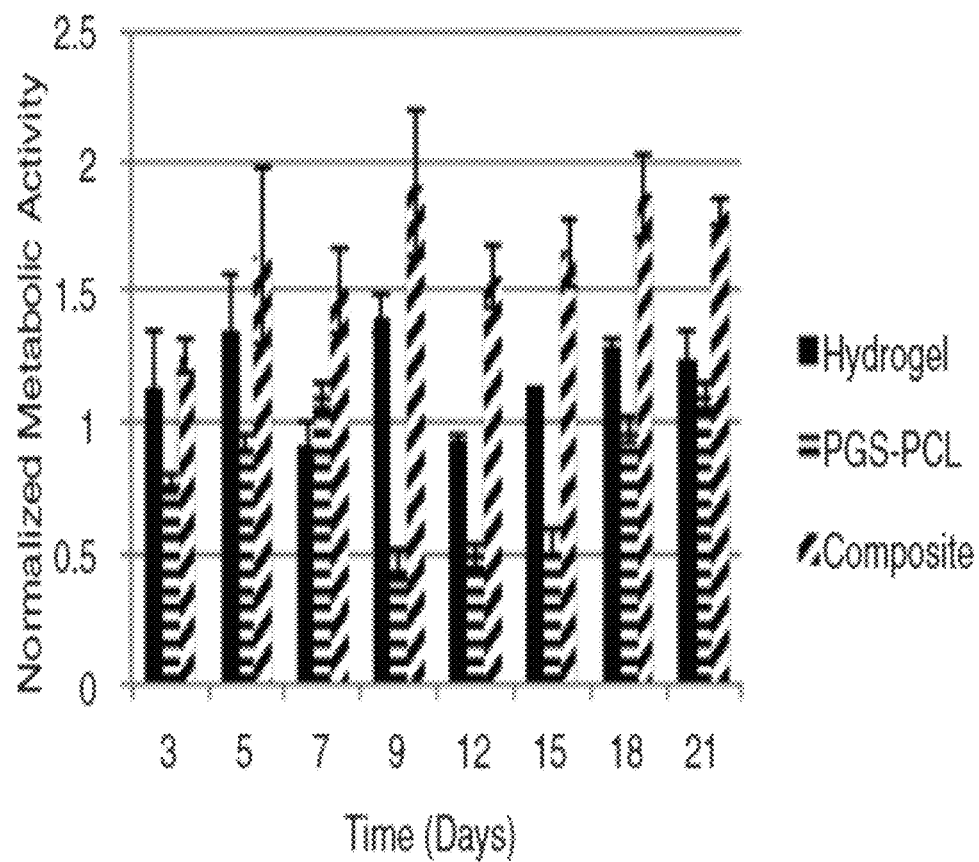
FIG. 11 is a graph illustrating the analysis of metabolic activity of fibroblast by Alamar Blue staining, according to one embodiment herein.

FIG. 11 is a graph illustrating the analysis of metabolic activity of fibroblast by Alamar Blue staining, according to one embodiment herein. The metabolic activity of seeded cells is used as an indirect method for determining cell number. The cells within the composite scaffolds illustrate high metabolic activity when compared to the cells present on PGS-PCL scaffolds or within the hydrogel scaffolds at all the time periods. The metabolic activity illustrates distinct peaks at various time periods for hydrogel scaffold, PGS-PCL scaffold and composite scaffold. This is caused by the fibroblast cells attaining a quiescent state when a certain cellular density is reached. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds.

Figure 12:
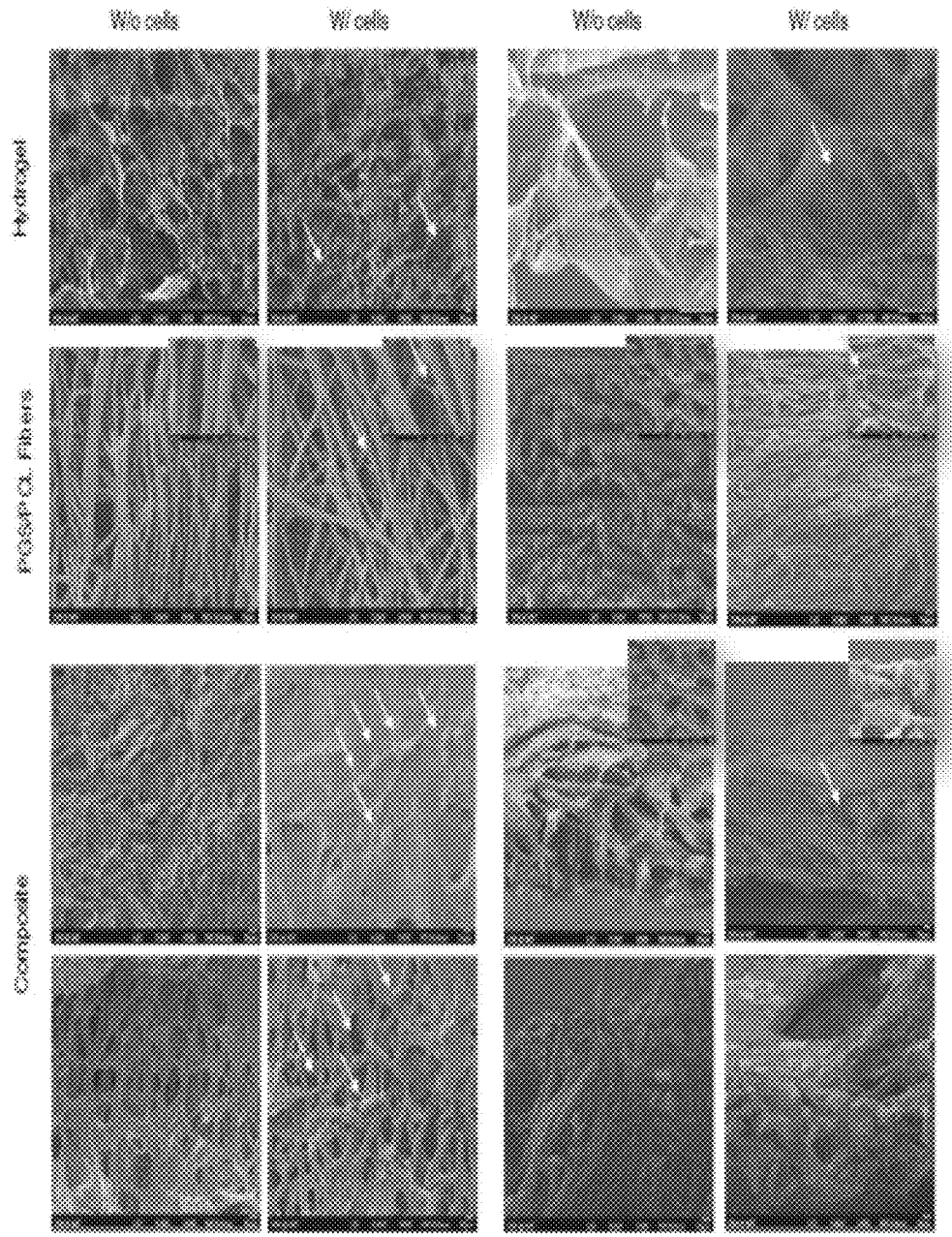
FIG. 12 is a surface electron microscope (SEM) image of the fibroblast seeded hydrogel scaffold, PGS-PCL scaffold and composite scaffold on day 21, according to one embodiment herein.

FIG. 12 is a surface electron microscope (SEM) image of the fibroblast seeded hydrogel scaffold, PGS-PCL scaffold and composite scaffold on day 21, according to one embodiment herein. The scaffolds are composite scaffold, PGS-PCL scaffold and hydrogel scaffold. The composite scaffold comprises hydrogel and poly (glycerol sebacate)-poly(ε-caprolactone) (PGS-PCL) microfibrous scaffolds. FIG. 12 illustrate a comparison between the hydrogel scaffold, PGS-PCL scaffold and composite scaffold with and without fibroblast scaffolds. The composite scaffold illustrates degradation of hydrogel scaffold. The cells remain on the fiber component after the degradation of hydrogel component in the composite scaffold. The fibroblasts are attached to the single fibers or bridged adjacent fibers within PGS-PCL scaffold.

According to one embodiment herein, the composite scaffold comprising hydrogel, micro-fibrous PGS-PCL scaffolds are efficient for fibroblast growth and distribution when compared with hydrogel scaffold and PGS-PCL scaffold for skin tissue engineering. The hydrogel component provides an extracellular mimicking environment. The hydrogel component provides efficiency for fibroblast cell delivery to scaffold. The fibrous PGS-PCL mesh allows the fibroblast cells to spread and distribute within the hydrogel. The fibrous PGS-PCL mesh provides mechanical properties to the weak hydrogel scaffolds.

According to one embodiment herein, addition of hydrogel component does not adversely affect the scaffold's mechanical properties based on similar values of Young's modulus and the ultimate tensile strength (UTS) of the bare PGS-PCL scaffolds and the composite scaffolds.

It is to be understood that the phraseology or terminology employed herein is for description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:
1. A method of fabricating composite scaffolds for skin tissue regeneration, the method comprises the steps of:
  synthesizing methacrylated hyaluronic acid (HAMA) and methacrylated gelatin (GelMA);
  synthesizing poly (glycerol sebacate)-poly(ε-caprolactone) (PGS-PCL) microfibrous scaffolds;
  synthesizing hydrogel (hydrogel precursor solution), and wherein the hydrogel is synthesized from methacrylated hyaluronic acid (HAMA) and methacrylated gelatin (GelMA);
  fabricating composite scaffold comprising hydrogel and poly (glycerol sebacate)-poly(ε-caprolactone) (PGS-PCL) microfibrous scaffolds;
  culturing fibroblast cells in predetermined conditions;
  encapsulating fibroblast cells within the composite scaffold comprising hydrogel and the poly (glycerol sebacate)-poly(ε-caprolactone) (PGS-PCL) microfibrous scaffolds and within the hydrogels separately, and wherein the hydrogel with encapsulated fibroblast cells is used to compare the fibroblast cell viability with composite scaffolds;
  seeding fibroblast cells on PGS-PCL scaffold separately, and wherein the PGS-PCL scaffold used to compare the fibroblast cell viability with composite scaffolds;
  soaking the poly (glycerol sebacate)-poly(ε-caprolactone) (PGS-PCL) microfibrous scaffolds and the poly(ε-caprolactone) (PCL) microfibers in the hydrogel precursor solution, and wherein the poly(ε-caprolactone) (PCL) microfibres are used as control reference/agents, and wherein the soaking of the hydrogel into the PGS-PCL microfibres is analysed and imaged to analyse the imbibition of hydrogel in the PGS-PCL microfibres and PCL microfibres;
  analysing a plurality of physico-chemical characteristics of the composite scaffold comprising hydrogel and poly (glycerol sebacate)-poly(ε-caprolactone) (PGS-PCL) microfibrous scaffolds, and wherein the physico-chemical characteristics comprises mechanical properties, swelling ratio and enzymatic degradation and a structural analysis by scanning electron microscope imaging; and analysing fibroblast cell viability, fibroblast cell attachment, fibroblast cell spreading, fibroblast cell proliferation and fibroblast cell metabolism in composite scaffolds, PGS-PCL scaffolds and hydrogels.

2. The method according to claim 1, wherein the step of synthesizing methacrylated hyaluronic acid (HAMA) and methacrylated gelatin (GelMA), comprises:
dissolving a predetermined amount of hyaluronic acid sodium salt in de-ionized water, and wherein the hyaluronic acid sodium salt is dissolved in de-ionized water to obtain a final concentration of 1% w/v, and wherein an optimum pH of the hyaluronic acid sodium salt and de-ionized water solution is monitored and maintained;
adding methacrylic anhydride dropwise to the solution comprising hyaluronic acid sodium salt and de-ionized water to obtain a solution mixture, and wherein a pH of 8 is maintained for the solution mixture of hyaluronic acid sodium salt, de-ionized water and methacrylic anhydride;
incubating the solution mixture on ice for a predetermined time period, and wherein the pH is monitored at regular interval of time, and wherein the pH of the solution mixture is maintained at 8;
agitating the solution mixture for 24 hours in a cold room, and wherein a temperature of the cold room is maintained at 4° C.;
dialyzing the solution mixture for two days in distilled water, and wherein a plurality of solutions are obtained from dialysis, and wherein the plurality of solutions obtained from dialysis are changed using 12-14 kDa molecular weight cut-off (MWCO) dialysis tubes;
lyophilizing the plurality of solutions for one week to obtain methacrylated hyaluronic acid; and
storing the methacrylated hyaluronic acid at −80° C.

3. The method according to claim 1, wherein the step of synthesizing metharylated gelatin (GelMA), comprises:
mixing porcine skin type A gelatin in Dulbecco's phosphate-buffered saline (DPBS) to obtain a gelatin solution;
incubating the gelatin solution at 60° C. for dissolving the porcine skin type A gelatin in Dulbecco's phosphate-buffered saline (DPBS);
adding methacrylated anhydride dropwise in the gelatin solution to obtain an emulsion, and wherein the methacrylated anhydride has a concentration of 0.8 ml/g;
agitating the emulsion comprising gelatin and methacrylic anhydride at a temperature of 60° C. for a time period of 1 hour;
adding warm DPBS to the emulsion for inhibiting a reaction within the emulsion to obtain a mixture, and wherein the temperature of DPBS is 40° C., and wherein the concentration of DPBS is 2×;
dialyzing the mixture comprising gelatin, methacrylic anhydride and DPBS for 1 week in distilled water using MWCO dialysis tubes, and wherein a plurality of solutions are obtained from dialysis;
freezing the plurality of solution obtained after dialysis for a period of 1 week to obtain a white and porous foam of metharylated gelatin (GelMA); and
incubating the foam of metharylated gelatin (GelMA) at a temperature of −80° C.

4. The method according to claim 1, wherein the step of synthesizing poly (glycerol sebacate)-poly(ε-caprolactone) (PGS-PCL) microfibrous scaffolds, comprises:
fabricating a frame, and wherein the frame comprises a copper wire covered with a non-adhesive tape with a glass slide on top;
dissolving poly (glycerol sebacate) and poly(ε-caprolactone) polymers in a predetermined ratio in an anhydrous chloroform-ethanol solvent to obtain a solution, and wherein the ratio of poly (glycerol sebacate) and poly(ε-caprolactone) is 2:1;
electrospinning the solution comprising poly (glycerol sebacate)-poly(ε-caprolactone) polymers and anhydrous chloroform-ethanol solvent at 12.5 kV, and wherein a concentration of total polymer is 33% w/v;
maintaining a distance of 10 cm between electrospinning needle and collector to obtain poly (glycerol sebacate)-poly(ε-caprolactone) (PGS-PCL) microfibrous scaffolds, and wherein dimensions of the needle is 21 gauge, and wherein a flow rate of 2 ml/hour is maintained in the elelctrospinning machine; and
drying the poly (glycerol sebacate)-poly(ε-caprolactone) (PGS-PCL) microfibrous scaffolds for 24 hours in a vacuum desiccator for removing residual solvents.

5. The method according to claim 1, wherein the step of synthesizing hydrogel (hydrogel precursor solution), comprises:
mixing methacrylated gelatin (GelMA) and methacrylated hyaluronic acid (HAMA) with a medium to obtain a solution;
adding a photoinitiator in the solution for obtaining a mixture, and wherein a concentration of the photoinitiator is 0.1% v/w, and wherein the photoinitiator crosslinks the solution, and wherein the photoinitiator is 2-hydroxy-1-(4-(hydroxyethoxy)phenyl)-2-methyl-1-propanone; and
exposing the mixture to UV light for a time period of 45 second at 2.6 mW/cm$^2$, and wherein a wavelength of UV light is 408 nm, wherein a hydrogel or hydrogel precursor solution is obtained with an initial solution volume of 20 μl, and wherein a diameter of the hydrogel is 6 mm, and wherein a thickness of the hydrogel is 0.5 mm, and wherein the hydrogel or hydrogel precursor is used for the synthesis/fabrication of composite scaffolds.

6. The method according to claim 1, wherein the step of fabricating composite scaffold comprising hydrogel and poly (glycerol sebacate)-poly(ε-caprolactone) (PGS-PCL) microfibrous scaffolds, comprises:
arranging the poly (glycerol sebacate)-poly(ε-caprolactone) (PGS-PCL) microfibrous scaffolds to obtain scaffolds of 6 mm diameter, and wherein the poly (glycerol sebacate)-poly(ε-caprolactone) (PGS-PCL) microfibrous scaffolds are arranged in sheets;
adding the hydrogel in the poly (glycerol sebacate)-poly(ε-caprolactone) (PGS-PCL) microfibrous scaffolds, and wherein an amount of the hydrogel is 20 ml, and wherein a concentration of the photoinitiator in the hydrogel is 0.1%, and wherein a poly (glycerol sebacate)-poly(ε-caprolactone) (PGS-PCL) microfibrous scaffolds absorb the hydrogel; and
exposing the poly (glycerol sebacate)-poly(ε-caprolactone) (PGS-PCL) microfibrous scaffolds and the hydrogel for crosslinking, and wherein the poly (glycerol sebacate)-poly(ε-caprolactone) (PGS-PCL) microfibrous scaffolds and the hydrogel are exposed to UV light for a time period of 45 second at 2.6 mW/cm$^2$, and wherein a wavelength of UV light is 408 nm, and wherein the composite scaffold comprises elelctrospun poly(glycerol sebacate)-poly(ε-caprolactone) (PGS- PCL) microfibrous scaffold within a hybrid hydrogel comprising methacrylated hyaluronic acid and methacrylated gelatin.

7. The method according to claim 1, wherein the step of encapsulating fibroblast cells within the composite scaffold comprising hydrogel and poly (glycerol sebacate)-poly(ε-caprolactone) (PGS-PCL) microfibrous scaffolds and hydrogels, comprises:
culturing fibroblast cells in a culture medium supplemented with 10% fetal bovine serum and 1% Penicillin-Streptomycin in predetermined atmospheric conditions, and wherein the predetermined atmospheric conditions comprises a temperature of 37° C. and carbon dioxide at a concentration of 5%, and wherein the fibroblast cells are cultured/grown on gelatin coated flasks, and wherein the fibroblast cells are passaged weekly;
trypsizinzing the fibroblast cells;
re-suspending the fibroblast cells in a hydrogel precursor solution at a predetermined concentration, and wherein the hydrogel precursor solution comprises methacrylated gelatin (GelMA) and methacrylated hyaluronic acid (HAMA) and photoinitiator, and wherein a concentration of photoinitiator is 0.1% w/v, and wherein a concentration of fibroblast cells suspended is $6 \times 10^6$ cells/ml;
exposing the composite scaffolds and the hydrogel precursor with fibroblast cells to UV light for a time period of 45 second at 2.6 mW/cm$^2$, and wherein the wavelength of UV light is 408 nm;
incubating the composite scaffolds and hydrogel precursor solution with fibroblast cells in a culture medium for a time period of 21 days in predetermined conditions, and wherein the composite scaffold comprises hydrogel and poly (glycerol sebacate)-poly(ε-caprolactone) (PGS-PCL) microfibrous scaffolds; and
changing the culture medium every 30 minutes for first two hours, and wherein the cultured medium is changed every 30 minutes for removing photoinitiator.

8. The method according to claim 1, wherein the step of seeding fibroblast cells on composite scaffold and PGS-PCL scaffold, comprises:
sterilizing the composite scaffolds and PGS-PCL scaffolds by immersion in 70% ethanol for 2 hours, and wherein the composite scaffold comprises poly (glycerol sebacate)-poly(ε-caprolactone) (PGS-PCL) microfibrous scaffolds and hydrogels;
exposing the sterilized composite scaffolds and the PGS-PCL scaffolds to UV radiation for a predetermined time period;
washing the sterilized composite scaffolds and the PGS-PCL scaffolds with DPBS medium;
selecting the fibroblast cells at a concentration of $2 \times 10^4$ cells/scaffold;
adding a predetermined volume of fibroblast cells suspension on the composite scaffolds and PGS-PCL scaffolds placed in a 48-well culture plate, and wherein the predetermined volume of fibroblast cells is 20 μl;
incubating the 48 well plate comprising the composite scaffolds and PGS-PCL scaffolds with fibroblast cell suspension for a time period of 1 hour, and wherein the fibroblast cells is attached to the composite scaffolds and PGS-PCL scaffolds in incubation; and
changing the culture medium every day.

9. The method according to claim 1, wherein the step of soaking the poly (glycerol sebacate)-poly(ε-caprolactone) (PGS-PCL) microfibrous scaffolds and the poly(ε-caprolactone) (PCL) fibres in the hydrogel precursor solution, comprises:
synthesizing PGS-PCL scaffolds and the PCL scaffolds, and wherein the size of the PGS-PCL scaffolds and PCL scaffolds is 6 mm diameter, and wherein the PCL scaffolds used as are negative control agents/reference;
adding 20 μl of the hydrogel solution on the PGS-PCL scaffolds and the PCL scaffolds; and
soaking the PGS-PCL fibres and the PCL fibres with hydrogel for a predetermined amount of time, and wherein the hydrogel with PGS-PCL fibres and the PCL fibres is imaged to analyse the imbibition of hydrogel in the PGS-PCL fibres and PCL fibres, and wherein the poly (glycerol sebacate) (PGL) component facilitates the penetration and imbibition of the hydrogel in the PGS-PCL microfibers, and wherein the PCL microfiber illustrate less absorption and imbibition of hydrogel when compared to the PGS-PCL microfibers, and wherein the imaging illustrates that the hydrogel penetrates into the PGS-PCL microfibers.

10. The method according to claim 1, wherein the analysis of a plurality of physico-chemical characteristics of the composite scaffold, PGS-PCL scaffold and hydrogel scaffold illustrate that the composite scaffold comprising hydrogel and poly (glycerol sebacate)-poly(ε-caprolactone) (PGS-PCL) microfibrous scaffolds has hydrophilic property, and wherein the hydrophilic property is imparted by the PGS-PCL component, and wherein the swelling ratio in the composite scaffold increased ($p<0.05$) after UV exposure.

11. The method according to claim 1, wherein the analysis of fibroblast cell viability, fibroblast cell attachment, fibroblast cell spreading, fibroblast cell proliferation and fibroblast cell metabolism in the composite scaffolds, PGS-PCL scaffolds and hydrogels illustrate that the fibroblast cells are spread in the composite hydrogel unevenly, and wherein the fibroblast cells are spread evenly in the hydrogel scaffold, and wherein the fibroblast cells are spread on the surface of PGS-PCL scaffold, and wherein the cell viability of fibroblast cell is above 90% in hydrogel, PGS-PCL scaffold and composite scaffolds, and wherein the fibroblast cells illustrate a high metabolic activity in composite scaffold when compared with the fibroblast cells present in PGS-PCL scaffold and hydrogel scaffold.

12. The method according to claim 1, wherein the hydrogel component of the composite scaffold provides an extracellular mimicking environment for fibroblast cells, and wherein the hydrogel component provides an ability of fibroblast cell delivery to an affected skin tissue, and wherein the PGS-PCL component of the composite scaffold facilitate a distribution of the fibroblast cells within the hydrogel component, and wherein the PGS-PCL component provides mechanical support to the composite scaffold.

* * * * *